United States Patent [19]
Cabib et al.

[11] Patent Number: 5,936,731
[45] Date of Patent: *Aug. 10, 1999

[54] METHOD FOR SIMULTANEOUS DETECTION OF MULTIPLE FLUOROPHORES FOR IN SITU HYBRIDIZATION AND CHROMOSOME PAINTING

[75] Inventors: Dario Cabib, Timrat; Robert A. Buckwald, Ramat Yishai; David Wine, Timrat; Yuval Garini, Mizpe Koranit; Nir Katzir, Givat Elah, all of Israel; Dirk G. Soeknsen, Carlsbad, Calif.; Moshe Lavi, Kiryat Chaim, Israel

[73] Assignee: Applied Spectral Imaging Ltd., Migdal Haemek, Israel

[ * ] Notice: This patent is subject to a terminal disclaimer.

[21] Appl. No.: 08/575,191

[22] Filed: Dec. 20, 1995

Related U.S. Application Data

[63] Continuation-in-part of application No. 08/571,047, Dec. 12, 1995, Pat. No. 5,784,162, which is a continuation-in-part of application No. 08/392,019, Feb. 21, 1995, Pat. No. 5,539,517, which is a continuation of application No. 08/107,673, Aug. 18, 1993, abandoned.

[30] Foreign Application Priority Data

Feb. 22, 1991 [IL] Israel .......................................... 97328
Feb. 19, 1992 [WO] WIPO ...................... PCT/US92/01171

[51] Int. Cl.⁶ ...................................................... G01B 9/02
[52] U.S. Cl. .................. 356/346; 250/339.02; 250/461.2
[58] Field of Search ...................................... 356/346, 300, 356/326; 250/339.02, 458.1, 459.1, 461.1, 461.2; 128/665; 382/128, 129, 133

[56] References Cited

U.S. PATENT DOCUMENTS

| | | |
|---|---|---|
| 4,930,516 | 6/1990 | Alfano et al. . |
| 4,976,542 | 12/1990 | Smith .................................... 356/346 |
| 5,377,003 | 12/1994 | Lewis et al. ............................. 356/346 |
| 5,432,865 | 7/1995 | Kasdan et al. . |
| 5,436,978 | 7/1995 | Kasdan et al. . |
| 5,539,517 | 7/1996 | Cabib ..................................... 356/346 |

OTHER PUBLICATIONS

Andersson–Engels et al, "Multicolor Fluorescence Imaging System for Tissue Diagnostics", SPIE vol. 1205 Bioimaging and Two Dimensional Spectroscopy, pp. 179–189 (1990).
Chamberlain, J. "the Principles of Interferomertric Spectroscopy", John Wiley & Sons pp. 16–18, 263.

(List continued on next page.)

Primary Examiner—Samuel A. Turner
Attorney, Agent, or Firm—Mark M. Friedman

[57] ABSTRACT

A fluorescent in situ hybridization method comprising the steps of (a) providing a cell nuclei having chromosomes hybridized with at least one nucleic acid probe including at least one nucleic acid molecule labeled with at least one fluorophore; (b) viewing the cell nuclei through a fluorescence microscope optically connected to an imaging spectrometer for obtaining a spectrum of each pixel of the cell nuclei by (i) collecting incident collimated light simultaneously from all pixels of the cell nuclei; (ii) passing the incident collimated light through an interferometer system so that the light is first split into two coherent beams and then recombine to interfere and form an exiting light beam; (iii) focusing the exiting light beam on a detector having an array of detector elements, so that at each instant each of the elements is the image of one and always the same pixel for the entire duration of the measurement and so that each of the elements produces a signal which is a particular linear combination of light intensity emitted by the pixel at different wavelengths; (iv) rotating or translating one or more of the elements of the interferometer, so that the optical path difference is scanned simultaneously for all the pixels of the cell nuclei; and (v) recording signals of each of the detector elements as function of time using a recording device to form a first spectral cube of data; and (c) interpreting the first spectral cube of data using a mathematical algorithm.

67 Claims, 14 Drawing Sheets

OTHER PUBLICATIONS

Wied, G. et al, "Computer Discrimination in Ectocervical Cells". Anal. And Quant Cytology, No. 3, vol. 3, Sep. 1981.

International Remote Imaging Systems (IRIS) News Release, Jul. 26, 1995.

Ried, T., "Fluoreszenz In Situ Hybridisierung in der Genetischen Diagnostik", 1994.

Wellman, J., "Imaging Spectrometers for Terresrial and Planetary Remote Sensing: A Progress Report", SPIE, vol. 750 Infrafred Systems and Components pp. 140–152 (1987).

Dozier, J., "HIRIS—The High Resolution Imaging Spectrometer", SPIE, vol. 924, pp. 23–30 (1988).

Valisa, P. et al, "Comparison and Applications to in–vivo Biology of Two Different Methods of Spectral Imaging: Confocal Scanning–Full Spectrum and Global Illumination Spectral Band–Pass Imaging", SPIE, vol. 2627, pp. 156–164, May 1995.

Maymon, P. et al, "Optical System Design Alternatives for the Moderate–Resolution Imaging Spectrometer–Tilt (MODIS–T) for the Earth Observing System (EOS)", SPIE, vol. 924, pp. 10–22 (1988).

(a)

(b)

FIG. 9 (a)
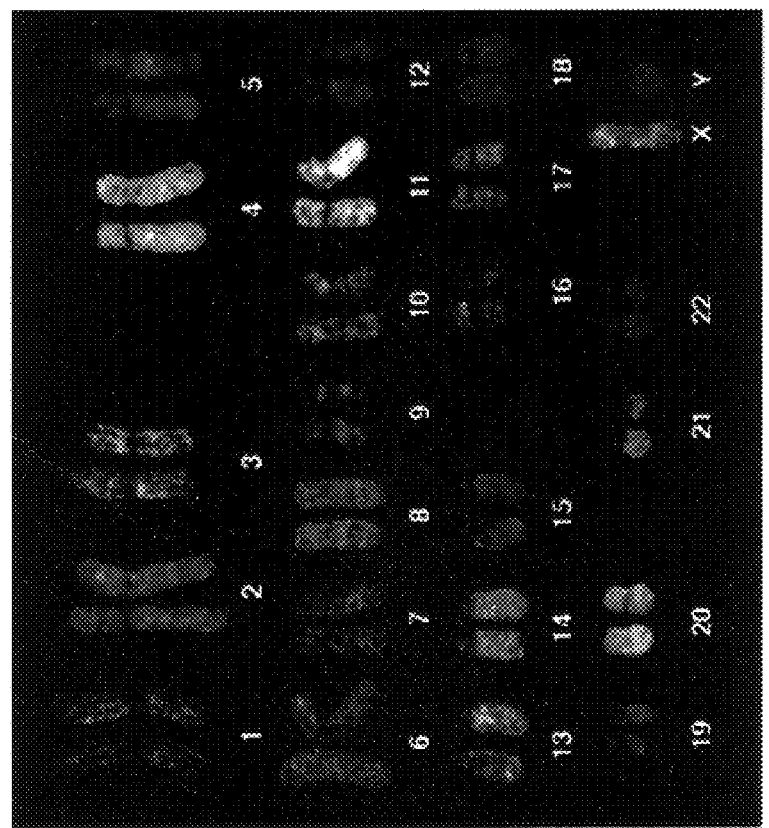
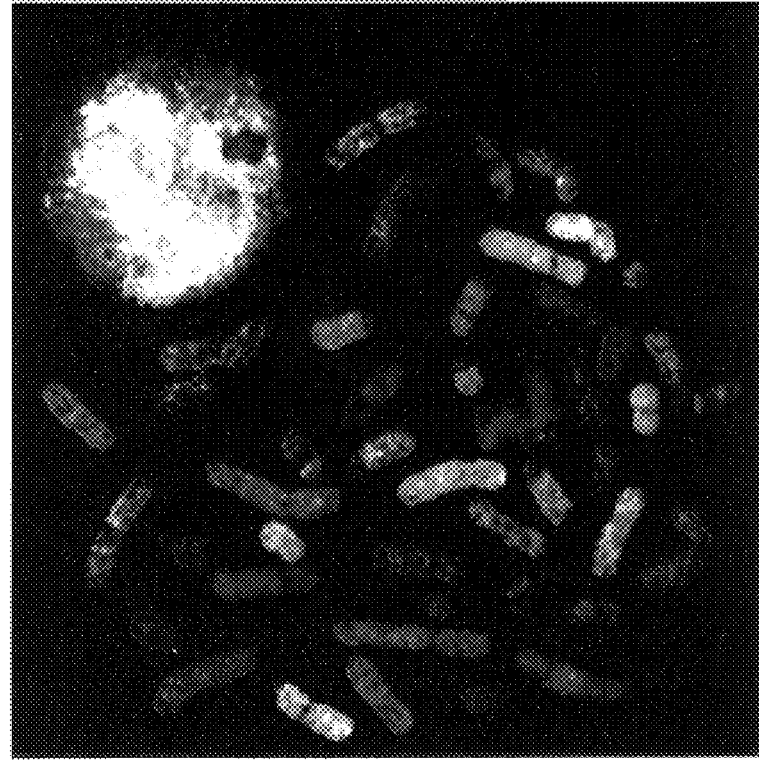
FIG. 9 (b)

METHOD FOR SIMULTANEOUS DETECTION OF MULTIPLE FLUOROPHORES FOR IN SITU HYBRIDIZATION AND CHROMOSOME PAINTING

This is a continuation in part of U.S. patent application Ser. No. 08/571,047 filed Dec. 12, 1995, now U.S. Pat. No. 5,784,162, which is a continuation-in-part U.S. patent application Ser. No. 08/392,019, filed Feb. 21, 1995 now U.S. Pat. No. 5,539,517, issued Jul. 23, 1996 which is a continuation of U.S. patent application Ser. No. 08/107,673, filed Aug. 18, 1993, now abandoned.

FIELD AND BACKGROUND OF THE INVENTION

The present invention relates in general to a method for simultaneous detection of multiple fluorophores. More particularly, the present invention relates to a spectral imaging method aimed at detecting and analyzing fluorescent in situ hybridizations employing numerous chromosome paints and/or loci specific probes each labeled with a different fluorophore or a combination of fluorophores, the method is highly sensitive both in spatial and spectral resolutions and is capable of simultaneous detection of dozens of flourophores and/or combinations of flourophores, therefore, the method of the present invention can be used for the detection of fluorescently painted complete sets of chromosomes and/or multiple loci from a species such as human and to provide a complete color karyotype.

A spectrometer is an apparatus designed to accept light, to separate (disperse) it into its component wavelengths, and measure the lights spectrum, that is the intensity of the light as a function of its wavelength. An imaging spectrometer is one which collects incident light from a scene and measures the spectra of each pixel (i.e., picture element) thereof Spectroscopy is a well known analytical tool which has been used for decades in science and industry to characterize materials and processes based on the spectral signatures of chemical constituents. The physical basis of spectroscopy is the interaction of light with matter. Traditionally, spectroscopy is the measurement of the light intensity emitted, transmitted, scattered or reflected from a sample, as a function of wavelength, at high spectral resolution, but without any spatial information.

Spectral imaging, on the other hand, which is a combination of high resolution spectroscopy and high resolution imaging (i.e., spatial information) has yet not been used for analyzing biological samples. The closest work so far described concerns either obtaining high spatial resolution information from a biological sample yet providing only limited spectral information, for example, when high spatial resolution imaging is performed with one or several discrete band-pass filters [See, Andersson-Engels et al. (1990) Proceedings of SPIE—Bioimaging and Two-Dimensional Spectroscopy, 1205, pp. 179–189], or alternatively, obtaining high spectral resolution (e.g., a full spectrum), yet limited in spatial resolution to a small number of points of the sample or averaged over the whole sample [See for example, U.S. Pat. No. 4,930,516, to Alfano et al.].

As will be described in great details below, combining spectroscopy with imaging is useful for various biological research and medical applications and is referred to hereinbelow as spectral bio-imaging. One example for the usefulness of spectral bio-imaging concerns detection of specific cellular constituents (e.g., proteins, nucleic acid sequences, etc.) after being labeled (i.e., tagged) with fluorescent probes. In this direction spectral imaging can be used to identify and map several fluorophores simultaneously in one measurement. In fact, the inherently high spectral resolution of spectral imaging of the present invention is ideally suited for 'sorting out' fluorescent probes (or other chemical constituents) with overlapping spectra.

Conceptually, a spectral bio-imaging system consists of (1) a measurement system, and (2) an analysis software. The measurement system includes all of the optics, electronics and the manner in which the sample is illuminated (e.g., light source selection), the mode of measurement (e.g., fluorescence), as well as the calibration best suited for extracting the desired results from the measurement. The analysis software includes all of the software and mathematical algorithms necessary to analyze and display important results in a meaningful way.

Spectral imaging has been used for decades in the area of remote sensing to is provide important insights in the study of Earth and other planets by identifying characteristic spectral absorption features. However, the high cost, size and configuration of remote sensing spectral imaging systems (e.g., Landsat, AVIRIS) has limited their use to air and satellite-borne applications [See, Maymon and Neeck (1988) Proceedings of SPIE—Recent Advances in Sensors, Radiometry and Data Processing for Remote Sensing, 924, pp. 10–22; Dozier (1988) Proceedings of SPIE—Recent Advances in Sensors, Radiometry and Data Processing for Remote Sensing, 924, pp. 23–30].

There are three basic types of spectral dispersion methods that might be considered for a spectral bio-imaging system: (i) spectral grating, (ii) spectral filters and (iii) interferometric spectroscopy. As will be described below, the latter is best suited to implement the method of the present invention.

In a grating (i.e., monochromator) based systems, also known as slit-type imaging spectrometers, such as for example the DILOR system: [see, Valisa et al. (September 1995) presentation at the SPEE Conference European Medical Optics Week, BiOS Europe '95, Barcelona, Spain], only one axis of a CCD (charge coupled device) array detector (the spatial axis) provides real imagery data, while a second (spectral) axis is used for sampling the intensity of the light which is dispersed by the grating as function of wavelength. The system also has a slit in a first focal plane, limiting the field of view at any given time to a line of pixels. Therefore, a full image can only be obtained after scanning the grating or the incoming beam in a direction parallel to the spectral axis of the CCD in a method known in the literature as line scanning. The inability to visualize the two-dimensional image before the whole measurement is completed makes it impossible to choose, prior to making a measurement, a desired region of interest from within the field of view and/or to optimize the system focus, exposure time, etc. Grating based spectral imagers are in use for remote sensing applications, because an airplane (or satellite) flying over the surface of the Earth provides the system with a natural line scanning mechanism.

It should be further noted that slit-type imaging spectrometers have a major disadvantage since most of the pixels of one frame are not measured at any given time, even though the fore-optics of the instrument actually collects incident light from all of them simultaneously. The result is that either a relatively large measurement time is required to obtain the necessary information with a given signal-to-noise ratio, or the signal-to-noise ratio (sensitivity) is substantially reduced for a given measurement time. Furthermore, slit-type spectral imagers require line scanning to collect the necessary information for the whole scene, which may introduce inaccuracies to the results thus obtained.

Filter based spectral dispersion methods can be further categorized into discrete filters and tunable filters. In these types of imaging spectrometers the spectral image is built by filtering the radiation for all the pixels of the scene simultaneously at a different wavelength at a time by inserting in succession narrow band filters in the optical path, or by electronically scanning the bands using acousto-optic tunable filters (AOTF) or liquid-crystal tunable filter (LCTF), see below. Similarly to the slit type imaging spectrometers equipped with a grating as described above, while using filter based spectral dispersion methods, most of the radiation is rejected at any given time. In fact, the measurement of the whole image at a specific wavelength is possible because all the photons outside the instantaneous wavelength being measured are rejected and do not reach the CCD. The sensitivity advantage that interferometric spectroscopy has over the filter and grating method is known in the art as the multiplex or Fellgett advantage.

Tunable filters, such as AOTFs and LCTFs have no moving parts and can be tuned to any particular wavelength in the spectral range of the device in which they are implemented. One advantage of using tunable filters as a dispersion method for spectral imaging is their random wavelength access; i.e., the ability to measure the intensity of an image at a number of wavelengths, in any desired sequence without the use of filter wheels. However, AOTFs and LCTFs have the disadvantages of (i) limited spectral range (typically, $\lambda_{max}=2\lambda_{min}$) while all other radiation that falls outside of this spectral range must be blocked, (ii) temperature sensitivity, (iii) poor transmission, (iv) polarization sensitivity, and (v) in the case of AOTFs an effect of shifting the image during wavelength scanning.

All these types of filter and tunable filter based systems have not been used successfully and extensively over the years in spectral imaging for any application, because of their limitations in spectral resolution, low sensitivity, and lack of easy-to-use and sophisticated software algorithms for interpretation and display of the data.

A method and apparatus for spectral analysis of images which have advantages in the above respects was disclosed in U.S. Pat. application Ser. No. 25 08/392,019 to Cabib et al., filed Feb. 21, 1995 now U.S Pat. No. 5,539,517, issued Jul. 23, 1996 which is incorporated by reference as if fully set forth herein, with the objective to provide a method and apparatus for spectral analysis of images which better utilizes all the information available from the collected incident light of the image to substantially decrease the required frame time and/or to substantially increase the signal-to-noise ratio, as compared to the conventional slit- or filter type imaging spectrometer and does not involve line scanning. According to this invention, there is provided a method of analyzing an optical image of a scene to determine the spectral intensity of each pixel thereof by collecting incident light from the scene; passing the light through an interferometer which outputs modulated light corresponding to a predetermined set of linear combinations of the spectral intensity of the light emitted from each pixel; focusing the light outputted from the interferometer on a detector array, scanning the optical path difference (OPD) generated in the interferometer for all pixels independently and simultaneously and processing the outputs of the detector array (the interferograms of all pixels separately) to determine the spectral intensity of each pixel thereof. This method may be practiced by utilizing various types of interferometers wherein the OPD is varied to build the interferograms by moving the entire interferometer, an element within the interferometer, or the angle of incidence of the incoming radiation. In all of these cases, when the scanner completes one scan of the interferometer, the interferograms for all pixels of the scene are completed. Apparatuses in accordance with the above features differ from the conventional slit- and filter type imaging spectrometers by utilizing an interferometer as described above, therefore not limiting the collected energy with an aperture or slit or limiting the incoming wavelength with narrow band interference or tunable filters, thereby substantially increasing the total throughput of the system. Thus, interferometer based apparatuses better utilize all the information available from the incident light of the scene to be analyzed, thereby substantially decreasing the measuring time and/or substantially increasing the signal-to-noise ratio (i.e., sensitivity). Consider, for example, the "whisk broom" design described in John B. Wellman (1987) Imaging Spectrometers for Terrestrial and Planetary Remote Sensing, SPIE Proceedings, Vol. 750, p. 140. Let n be the number of detectors in the linear array, m×m the number of pixels in a frame and T the frame time. The total time spent on each pixel in one frame summed over all the detectors of the array is $nT/m^2$. By using the same size array and the same frame rate in a method according to the invention described in U.S. Pat. No. 5,539,517, the total time spent summed over all the detectors on a particular pixel is the same, $nT/m^2$. However, whereas in the conventional grating method the energy seen by every detector at any time is of the order of 1/n of the total, because the wavelength resolution is 1/n of the range, in a method according to the invention described in U.S. Pat. No. 5,539,517 the energy is of the order of unity because the modulating function is an oscillating function (e.g., sinusoidal (Michelson) or similar periodic function such as low finesse Airy function with Fabry-Perot) whose average over a large OPD range is 50%. Based on the standard treatment of the Fellgett advantage (or multiplex advantage) described in interferometry textbooks [for example, see, Chamberlain (1979) The principles of interferometric spectroscopy, John Wiley and Sons, pp. 16–18 and p. 263], it is possible to show that devices according to this invention have measurement signal-to-noise ratios which are improved by a factor of $n^{0.5}$ in the cases of noise limitations in which the noise level is independent of signal (system or background noise limited situations) and by the square root of the ratio of the signal at a particular wavelength to the average signal in the spectral range, at wavelengths of a narrow peak in the cases the limitation is due to signal photon noise. Thus, according to the invention described in U.S. Pat. No. 5,539,517 all the required OPDs are scanned simultaneously for all the pixels of the scene in order to obtain all the information required to reconstruct the spectrum, so that the spectral information is collected simultaneously with the imaging information. This invention can be used with many different optical configurations, such as a telescope for remote sensing, a microscope for laboratory analysis, fiber optics for industrial monitoring and medical imaging, diagnosis, therapy and others.

In a continuation application (U.S. Pat. application Ser. 08/571,046, to Cabib et al., filed Dec. 12, 1995 which is incorporated by reference as if fully set forth herein) the objective was to provide spectral imaging methods for biological research, medical diagnostics and therapy, which methods can be used to detect spatial organization (i.e., distribution) and to quantify cellular and tissue natural constituents, structures, organelles and administered components such as tagging probes (e.g., fluorescent probes) and drugs using light transmission, reflection, scattering and fluorescence emission strategies, with high spatial and spectral resolutions. In U.S. patent application Ser. No. 08/571, 047, the use of the spectral imaging apparatus described in U.S. Pat. No. 5,539,517 for interphase fluorescent in situ hybridization of as much as six loci specific probes (each loci located on a different chromosome) was demonstrated, as well as additional biological and medical applications.

Spectral bio-imaging systems are potentially useful in all application in which subtle spectral differences exist between chemical constituents whose spatial distribution and organization within an image are of interest. The measurement can be carried out using virtually any optical system attached to the system described in U.S. Pat. No. 5,539,517, for example, a fluorescence microscope combined with administered fluorescent fluorophores or combinations of fluorophores.

Fluorescence measurements can be made with any standard filter cube (consisting of a barrier filter, excitation filter and a dichroic mirror), or any customized filter cube or combinations of filter cubes for special applications, provided the emission spectra fall within the spectral range of the system sensitivity.

One of the major benefits of the Human Genome Project (HGP) has been the isolation of a large number of nucleic acid probes for diseased genes and other chromosome regions and structures. This has stimulated interest in DNA diagnostics as the number and types of tests that can be developed is dependent upon these probes. In recent years there has been particular interest in fluorescent in situ hybridization (FISH) which is the process of marking with a fluorescent moiety conjugated to a specific nucleic acid molecule complementary to an examined chromosome region (collectively referred herein as a probe), followed visualization of the fluorescent moiety by fluorescence microscopy.

There is a clear trend for employing FISH technology in the clinic in parallel to its traditional employment in the basic research laboratory. FISH may be considered an advanced approach to cytogenetics and it is clear that the amount of information about chromosomes that may be gained from FISH far outdistances that obtained from standard karyotyping by DNA banding methods. In addition, diagnostics information may be gained much more rapidly using techniques such as interphase cytogenetics as compared to classical (metaphase) cytogenetics.

According to the present invention provided is a FISH imaging method, capable of simultaneously acquire fluorescence spectra from all pixels of a field of view of a fluorescence microscope and simultaneously detect the location of dozens of probes in a single measurement. In conjunction with the availability of chromosome specific probes (i.e., chromosome paints) and novel labeling strategies, the method is able to create a FISH karyotype with each chromosome being painted with a different color (i.e., 24 different colors for a human male karyotype, 23 for a female). This method results in extremely high sample throughput and allows analysis of an essentially unlimited number of probes.

There is thus a widely recognized need for, and it would be highly advantageous to have a spectral imaging method for detecting and analyzing fluorescent in situ hybridizations employing numerous chromosome paints and/or loci specific probes each labeled with a different fluorophore or a combination of fluorophores for the detection of fluorescently painted complete sets of chromosomes and/ or multiple loci from a species such as human.

SUMMARY OF THE INVENTION

According to the present invention there is provided a spectral imaging method aimed at detecting and analyzing fluorescent in situ hybridizations employing numerous chromosome paints and/or loci specific probes each labeled with a different fluorophore or a combination of fluorophores, the method is highly sensitive both in spatial and spectral resolutions and is capable of simultaneous detection of dozens of flourophores and/or combinations of flourophores and thus can be used for the detection of fluorescently painted complete sets of chromosomes and/or multiple loci from a species such as human and to provide a color karyotype.

According to further features in preferred embodiments of the invention described below, the method comprising the steps of (a) preparing a sample to be spectrally imaged; (b) viewing the sample through an optical device, the optical device being optically connected to an imaging spectrometer, the optical device and the imaging spectrometer being for obtaining a spectrum of each pixel of the sample by (i) collecting incident light simultaneously from all pixels of the sample using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the sample for the entire duration of the measurement so that the real image of the sample is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) rotating or translating (i.e., scanning) one or more of the elements of the interferometer system, so that the optical path difference between the two coherent beams generated by the interferometer system is scanned simultaneously for all the pixels of the sample; and (v) recording signals of each of the detector elements as function of time using a recording device to form a first spectral cube of data; and (c) interpreting the first spectral cube of data using a mathematical algorithm.

According to still further features in the described preferred embodiments the method further comprising the step of (d) displaying a map of the interpreted spectral cube of data.

According to still further features in the described preferred embodiments the optical device is a fluorescence microscope.

According to still further features in the described preferred embodiments the collimated light is a fluorescence light emitted from the sample.

According to still further features in the described preferred embodiments the collimated light emitted from the sample is an administered probe fluorescence.

According to still further features in the described preferred embodiments the light originates from a source such as laser, white light, filtered light, ultraviolet light or a light having a small wavelength range.

According to still further features in the described preferred embodiments the light originates from a multiplicity of light sources, the sources operate simultaneously or successively.

According to still further features in the described preferred embodiments the two-dimensional array is selected from the group consisting of a video rate CCD, a cooled high dynamic range CCD, an intensified CCD and a time gated intensified CCD.

According to still further features in the described preferred embodiments the sample is a cell during interphase, a cell during mitosis and/or a cell during meiosis.

According to still further features in the described preferred embodiments the cell is from a human.

According to still further features in the described preferred embodiments the cell is a cancerous cell, a blood cell, a fetal cell or a cell suspected of being malignant.

According to still further features in the described preferred embodiments the sample is a cell, the light is induced by a probe, the probe binds to a specific cellular constituent, the method is for detecting the presence or the level of the cellular constituent.

According to still further features in the described preferred embodiments the probe includes a conjugated fluorescent moiety and the induction is a fluorescence light emission of the fluorescent moiety.

According to still further features in the described preferred embodiments the probe further includes a nucleic acid molecule, the method is for detecting the presence or the level of a cellular nucleic acid hybridizing with the nucleic acid molecule.

According to still further features in the described preferred embodiments the cellular nucleic acid is deoxyribonucleic acid and/or ribonucleic acid.

According to still further features in the described preferred embodiments the fluorescent moiety is SPECTRUMORANGE and SPECTRUMORANGE, are rhodamine and flurescein derivatives respectively, Aqua, Texas-Red, FITC, rhodamine, fluorescein, cascade blue and/or any combination thereof.

According to still further features in the described preferred embodiments the mathematical algorithm is a point operation analysis of the spectrum of each of the pixels in the sample.

According to still further features in the described preferred embodiments the point operation analysis includes mapping the spectrum of each of the pixels in the sample into a scalar according to a transformation function.

According to still further features in the described preferred embodiments the point operation analysis includes mapping the spectrum of each of the pixels of the sample into another spectrum according to a transformation function.

According to still further features in the described preferred embodiments the mathematical algorithm is a morphological analysis.

According to still further features in the described preferred embodiments the mathematical algorithm is a similarity mapping analysis for computing for each of the pixels in the sample a spectral difference from a reference spectrum.

According to still further features in the described preferred embodiments the similarity mapping analysis results in generating a gray level or a pseudocolor image, in which bright pixels correspond to a small spectral difference and dark pixels correspond to a large spectral difference.

According to still further features in the described preferred embodiments the similarity mapping analysis results in generating a gray level or a pseudocolor image, in which bright pixels correspond to a large spectral difference and dark pixels correspond to a small spectral difference.

According to still further features in the described preferred embodiments the spectral difference is a scalar defined as the integral over a predefined wavelength range of the absolute value of the difference between the spectrum of each of the pixels and the reference spectrum.

According to still further features in the described preferred embodiments the mathematical algorithm is a classification mapping analysis computing for the spectrum of each of the pixels a spectral difference from several reference spectra.

According to still further features in the described preferred embodiments the classification mapping analysis results in generating a multicolor image, in which groups of pixels having a predetermined maximal spectral differences from one of the several reference spectra are colored with a predetermined artificial color.

According to still further features in the described preferred embodiments the spectral difference is a scalar defined as the integral over a predefined wavelength range of the absolute value of the difference between the spectrum of each of the pixels and one of the several reference spectra.

According to still further features in the described preferred embodiments the mathematical algorithm is a principal component analysis.

According to still further features in the described preferred embodiments the principal component analysis includes (a) building a covariant matrix for all of the pixels and the wavelengths of the measurement, including wavelengths of exciting sources when multiple wavelengths are used; (b) diagonalizing the covariant matrix and finding all independent orthogonal spectral base elements; (c) finding which of the base elements tag certain features in the sample.

According to still further features in the described preferred embodiments the mathematical algorithm is a linear combination analysis.

According to still further features in the described preferred embodiments the linear combination analysis includes applying an arithmetical function between corresponding wavelengths of corresponding pairs of pixels belonging to the first spectral cube of data and to a second spectral cube of data, to obtain a resulting third spectral cube of data.

According to still further features in the described preferred embodiments the linear combination analysis is for a purpose such as averaging two spectral cubes of data or time changes follow-up and spectral normalization.

According to still further features in the described preferred embodiments the linear combination analysis includes applying a given scalar to every wavelength of the spectra of each of the pixels by an arithmetical function, the function is addition, subtraction, multiplication, division and/or combinations thereof.

According to still further features in the described preferred embodiments the linear combination analysis is for background subtraction in which a spectrum of a pixel located in a background region of the sample is subtracted from the spectra of the pixels of the sample.

According to still further features in the described preferred embodiments the linear combination analysis is for a calibration procedure in which a spectrum measured prior to the viewing the sample is for dividing the spectra of the pixels of the sample.

According to still further features in the described preferred embodiments the mathematical algorithm is an optical density analysis.

According to still further features in the described preferred embodiments the optical density analysis is for obtaining an interpreted image which is an optical density map.

According to still further features in the described preferred embodiments the mathematical algorithm computes a Red-Green-Blue color image using predefined wavelength ranges.

According to still further features in the described preferred embodiments the Red-Green-Blue color image is modified by a contrast stretching algorithm.

According to still further features in the described preferred embodiments the Red-Green-Blue color image is modified by a contrast stretching algorithm.

According to still further features in the described preferred embodiments the mathematical algorithm computes a ratio between intensities at two different wavelengths for each of the spectra of the pixels.

According to still further features in the described preferred embodiments the mathematical algorithm computes a ratio between intensities at two different wavelengths for each of the spectra of the pixels and paints each of the pixels in a lighter or darker artificial color, according to the computed ratio.

According to still further features in the described preferred embodiments the method is for spectral identification of multiple fluorophores administered to the sample.

According to still further features in the described preferred embodiments described below the method is a fluorescent in situ hybridization method comprising the steps of (a) providing a cell nuclei having chromosomes, the chromosomes being hybridized with at least one nucleic acid probe, each of the at least one nucleic acid probe including at least one nucleic acid molecule, each of the at least one nucleic acid molecule being labeled with at least one fluorophore; (b) viewing the cell nuclei through a fluorescence microscope, the fluorescence microscope being optically connected to an imaging spectrometer, the fluorescence microscope and the imaging spectrometer being for obtaining a spectrum of each pixel of the cell nuclei by (i) collecting incident light simultaneously from all pixels of the cell nuclei using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the cell nuclei for the entire duration of the measurement, so that the real image of the cell nuclei is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) rotating or translating (i.e., scanning) one or more of the elements of the interferometer system, so that the optical path difference between the two coherent beams generated by the interferometer system is scanned simultaneously for all the pixels of the cell nuclei; and (v) recording signals of each of the detector elements as function of time using a recording device to form a first spectral cube of data; and (c) interpreting the first spectral cube of data using a mathematical algorithm.

According to still further features in the described preferred embodiments the at least one nucleic acid molecule is at least one locus, at least one fragmented chromosome, at least one yeast artificial chromosome including an insert, at least one plasmid including an insert, at least one cosmid including an insert, at least one phagemid including an insert, at least one viral vector including an insert, a complete genome of a species, a complete genome of a cancerous tissue and/or combinations thereof.

According to still further features in the described preferred embodiments the at least one fluorophore is at least one fluorescent combinatorial dye.

According to still further features in the described preferred embodiments the cell nuclei is a cell nuclei during interphase, a cell nuclei during mitosis and/or a cell nuclei during meiosis.

According to still further features in the described preferred embodiments the number of nucleic acid probes is one, two, three, four, five, six, seven, eight, nine, ten, eleven, twelve, thirteen, fourteen, fifteen, sixteen, seventeen, eighteen, nineteen, twenty, twenty one, twenty two, twenty three, twenty four or higher than twenty four, each of the probes includes a different fluorophore or a different combination of the fluorophores.

According to still further features in the described preferred embodiments the chromosomes are interphase chromosomes, chromosomes during mitosis and chromosomes during meiosis.

According to still further features in the described preferred embodiments the mathematical algorithm is a point operation analysis of the spectrum of each of the pixels in the cell nuclei.

According to still further features in the described preferred embodiments the point operation analysis includes mapping the spectrum of each of the pixels in the cell nuclei into a scalar according to a transformation function.

According to still further features in the described preferred embodiments the point operation analysis includes mapping the spectrum of each of the pixels of the cell nuclei into another spectrum according to a transformation function.

According to still further features in the described preferred embodiments the mathematical algorithm is a morphological analysis, the morphological analysis determines the relative size of the chromosomes in the cell nuclei.

According to still further features in the described preferred embodiments the mathematical algorithm is a classification mapping analysis computing for the spectrum of each of the pixels a spectral difference from at least one reference spectrum.

According to still further features in the described preferred embodiments the classification mapping analysis results in generating a multicolor image, in which groups of pixels having a predetermined maximal spectral differences from one of the several reference spectra are colored with a predetermined artificial color.

According to still further features in the described preferred embodiments the spectral difference is a scalar defined as the integral over a predefined wavelength range of the absolute value of the difference between the spectrum of each of the pixels and one of the several reference spectra.

According to still further features in the described preferred embodiments the mathematical algorithm is a principal component analysis.

According to still further features in the described preferred embodiments the principal component analysis includes (a) building a covariant matrix for all of the pixels and the wavelengths of the measurement, including wavelengths of exciting sources when multiple wavelengths are used; (b) diagonalizing the covariant matrix and finding all independent orthogonal spectral base elements; (c) finding which of the base elements or a combination thereof tag certain features in the cell nuclei.

According to still further features in the described preferred embodiments the mathematical algorithm is a linear combination analysis.

According to still further features in the described preferred embodiments the linear combination analysis is for spectral normalization.

According to still further features in the described preferred embodiments the linear combination analysis includes applying a given scalar to every wavelength of the spectra of each of the pixels by an arithmetical function, the function is addition, subtraction, multiplication, division and/or combinations thereof.

According to still further features in the described preferred embodiments the linear combination analysis is for background subtraction in which a spectrum of a pixel located in a background region of the cell nuclei is subtracted from the spectra of the pixels of the cell nuclei.

According to still further features in the described preferred embodiments the linear combination analysis is for a calibration procedure in which a spectrum measured prior to the viewing the cell nuclei is for dividing the spectra of the pixels of the cell nuclei.

According to still further features in the described preferred embodiments the mathematical algorithm computes a Red-Green-Blue color image using predefined wavelength ranges.

According to still further features in the described preferred embodiments the mathematical algorithm computes a ratio between intensities at two different wavelengths for each of the spectra of the pixels.

According to still further features in the described preferred embodiments the mathematical algorithm computes a ratio between intensities at two different wavelengths for each of the spectra of the pixels and paints each of the pixels in a lighter or darker artificial color, according to the computed ratio.

According to still further features in the described preferred embodiments the method is for an application such as providing a color karyotype of embryonic cells, providing a color karyotype of white blood cells, providing a color karyotype of malignant cells and/or providing a color karyotype of cells examined for malignancy.

According to still further features in the described preferred embodiments the embryonic cells are chorionic villi cells and/or embryonic cells isolated from a pregnant woman peripheral blood.

According to still further features in the described preferred embodiments the method is for detecting a trisomy of human chromosome 21, human chromosomal band 21$q$22, a fragment of human chromosomal band 21$q$22, human chromosome 18, a fragment of human chromosome 18, human chromosome 13 and a fragment of human chromosome 13.

According to still further features in the described preferred embodiments the providing the color karyotype of the cells examined for malignancy is for obtaining a color translocation map.

According to still further features in the described preferred embodiments providing the color karyotype of the malignant cells is for obtaining a color translocation map.

The present invention successfully addresses the shortcomings of the presently known configurations by providing a method for in situ hybridization which is sensitive enough to simultaneously detect dozens of spectrally similar, yet some what different fluorescent probes, thus, the method of the present invention is capable of providing a color karyotype in which each chromosome pair appears in a different RGB or artificial color; simultaneous loci mapping of dozens of loci; a combination of color karyotyping and multiple loci mapping and readily available genetic inspection for chromosomal aberrations.

BRIEF DESCRIPTION OF THE DRAWINGS

The file of this patent contains at least one drawing executed in color. Copies of this patent with color drawing (s) will be provided by the Patent and Trademark Office upon request and payment of necessary fee.

The invention herein described, by way of example only, with reference to the accompanying drawings, wherein:

FIGS. 9a and 9b are color presentations of FIGS. 8a and 8b, respectively;

DESCRIPTION OF THE PREFERRED EMBODIMENTS

The present invention is of a spectral imaging method for detecting and analyzing fluorescent in situ hybridizations employing numerous chromosome paints and/or loci specific probes each labeled with a different fluorophore or a combination of fluorophores, the method is highly sensitive both in spatial and spectral resolutions and is capable of simultaneous detection of dozens of flourophores or combinations of flourophores, therefore, the method of the present invention can be used for the detection of fluorescently painted complete sets of chromosomes and/or multiple loci from a species such as human and to provide a color karyotype.

Figure 1:
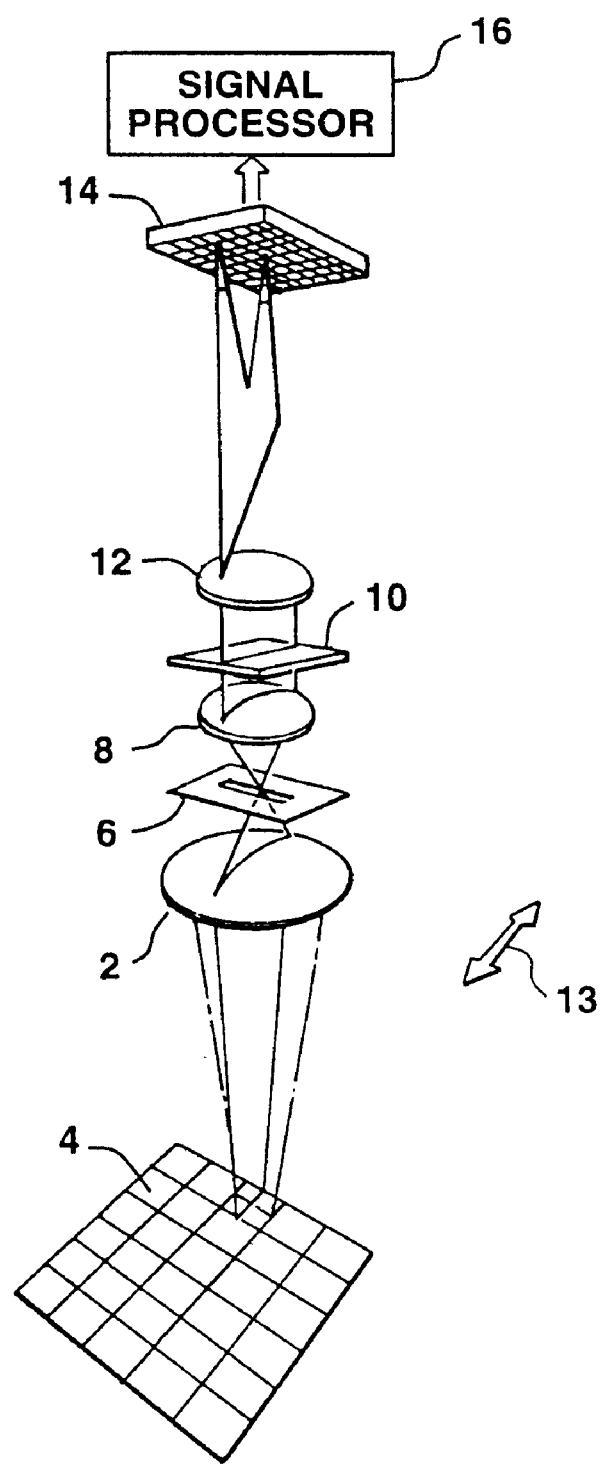
FIG. 1 illustrates a conventional (prior art) slit-type imaging spectrometer.

For purposes of better understanding the present invention, as illustrated in FIGS. 4–9 of the drawings, reference is first made to the construction and operation of a conventional (i.e., prior art) slit-type imaging spectrometer utilizing a two-dimensional array of detectors as illustrated in FIG. 1.

Thus, the prior art slit-type imaging spectrometer as illustrated in FIG. 1 comprises a collection optical system as indicated at 2, for collecting the incident light from a scene, schematically indicated at 4 and focusing the substantially parallel light of the scene 4 onto a first focal plane occupied by a slit 6 to define the field of view. The light exiting from slit 6 is collimated in a collimator lens 8 and is passed through a spectral dispersion element 10 (e.g., a grating) to separate the various wavelengths. The output from spectral dispersion element 10 is focused by a focusing lens 12 onto a two-dimensional detector array 14 in a second focal plane. The output of detector array 14 is fed to a signal processor 16.

In the two-dimensional array of detectors 14 illustrated in the prior art imaging spectrometer of FIG. 1, the movement of the system (e.g., a raster movement or line scanning indicated by arrow 13) effects the scanning along one dimension. The scanning along the second dimension is effected by the slit 6 which is oriented perpendicularly to the direction of movement of the system. The slit 6 thus assures that each detector within the array 14 sees only the contribution of one pixel at a single wavelength at any time. This is necessary to separate the spectra of each pixel.

As mentioned in the background section and hereinabove, the disadvantage of the prior art method illustrated in FIG. 1 is that most of the pixels of one frame are not measured at any given time even though the optical system 2 actually collects energy from all of them simultaneously. As a result, the required frame time is significantly increased, and/or the signal-to-noise ratio (sensitivity) is substantially decreased with respect to a system which does not have the need for such a slit.

Figure 2:
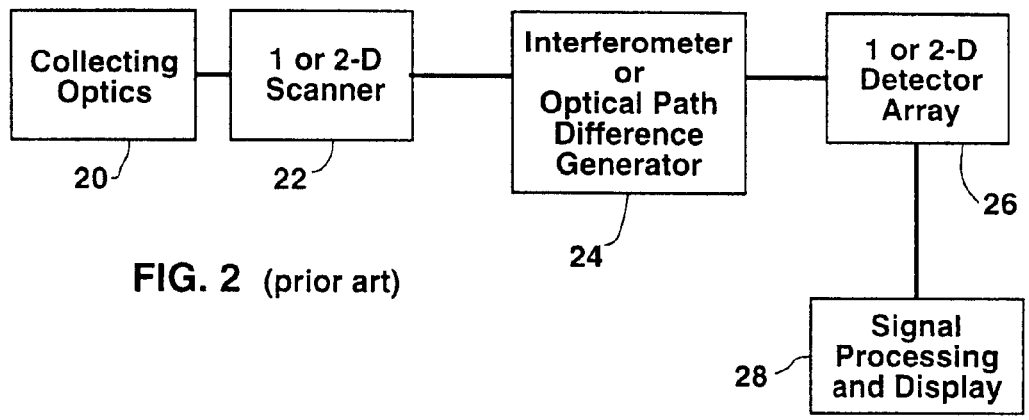
FIG. 2 is a block diagram illustrating the main components of an imaging spectrometer constructed in accordance with U.S. Pat. No. 5,539,517 (prior art)

FIG. 2 is a block diagram illustrating the main components of an improved prior art imaging spectrometer disclosed in U.S. Pat. No. 5,539,517 to Cabib et al., which is incorporated by reference as if fully set forth herein. This imaging spectrometer is constructed highly suitable to implement the methods of the present invention.

Thus, the prior art imaging spectrometer of FIG. 2 includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously for all the pixels of the field of view, in order to obtain all the information required to reconstruct the spectrum. The spectra of all the pixels in the scene are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517, alternative types of interferometers may be employed. These include (1) a moving type interferometer in which the OPD is varied to modulate the light, namely, a Fabry-Perot interferometer with scanned thickness; (2) a Michelson type interferometer which includes a beamsplitter receiving the beam from an optical collection system and a scanner, and splitting the beam into two paths; (3) a Sagnac interferometer optionally combined with other optical means in which interferometer the OPD varies with the angle of incidence of the incoming radiation, and (4) a four-mirror plus beamsplitter interferometer as further described in the cited U.S. patent application.

Figure 3:
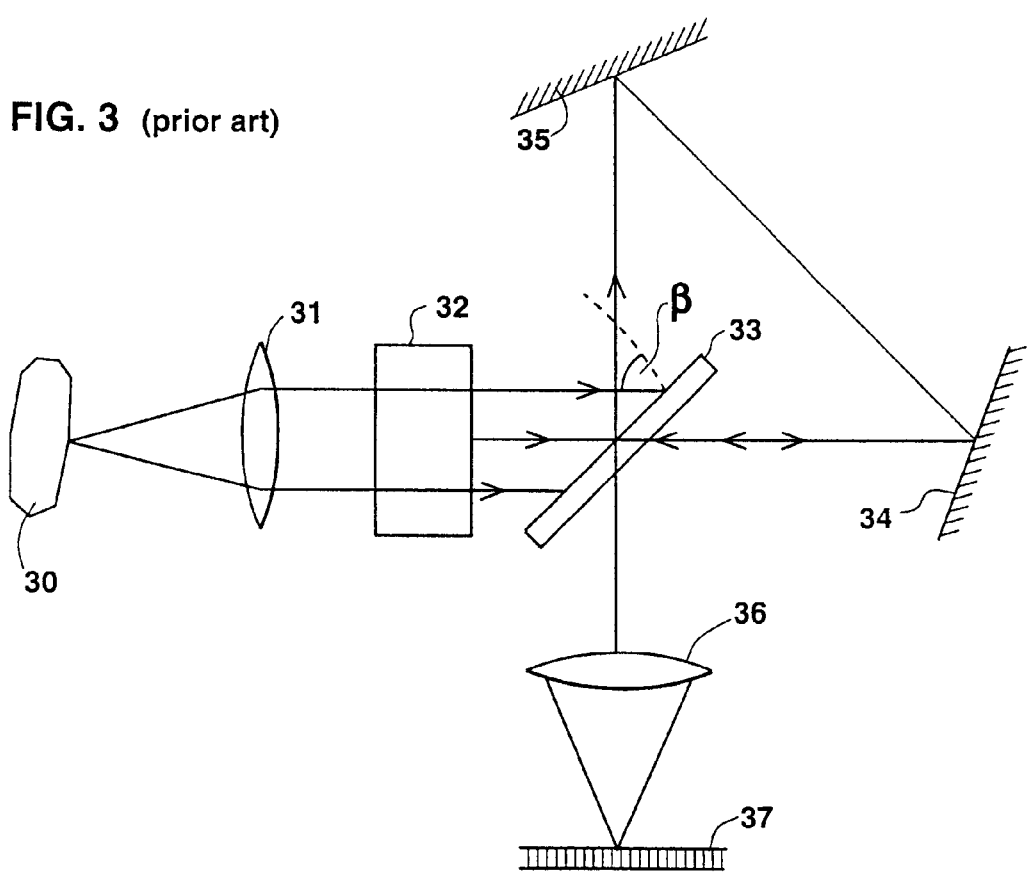
FIG. 3 illustrates a non-moving type interferometer, namely, a Sagnac interferometer, as used in an imaging spectrometer in accordance with U.S. Pat. No. 5,539,517 (prior art)

FIG. 3 illustrates an imaging spectrometer constructed in accordance with U.S. Pat. No. 5,539,517 utilizing an interferometer in which the OPD varies with the angle of incidence of the incoming radiation. A beam entering the interferometer at a small angle to the optical axis undergoes an OPD which varies substantially linearly with this angle.

In the interferometer of FIG. 3, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

At the end of one scan, every pixel has been measured through all the OPD's, and therefore the spectrum of each pixel of the scene can be reconstructed by Fourier transformation. A beam parallel to the optical axis is compensated, and a beam at an angle (θ) to the optical axis undergoes an OPD which is a function of the thickness of the beamsplitter 33, its index of refraction, and the angle θ. The OPD is proportional to θ for small angles. By applying the appropriate inversion, and by careful bookkeeping, the spectrum of every pixel is calculated.

In the configuration of FIG. 3 the ray which is incident on the beamsplitter at an angle β(β=45° in FIG. 3) goes through the interferometer with an OPD=0, whereas a ray which is incident at a general angle β−θ undergoes an OPD given by the following:

$$\text{OPD}(\beta, \theta, t, n) = t[(n^2 - \sin^2(\beta + \theta))^{0.5} - (n^2 - \sin^2(\beta - \theta))^{0.5} + 2\sin\beta\sin\theta] \quad (1)$$

where β is the angle of incidence of the ray on the beamsplitter; θ is the angular distance of a ray from the optical axis or interferometer rotation angle with respect to the central position; t is the thickness of the beamsplitter; and n is the index of refraction of the beamsplitter.

It follows from Equation 1 that by scanning both positive and negative angles with respect to the central position, one can get a double-sided interferogram for every pixel, which helps eliminate phase errors giving more accurate results in the Fourier transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact, according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Thus, imaging spectrometers constructed in accordance with the invention disclosed in U.S. Pat. No. 5,539,517 do not merely measure the intensity of light coming from every pixel in the field of view, but also measure the spectrum of each pixel in a predefined wavelength range. They also better utilize all the radiation emitted by each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including medical diagnostic and therapy and biological research applications, as well as remote sensing for geological and agricultural investigations, and the like.

An imaging spectrometer in accordance with the invention disclosed in U.S. Pat. No. 5,539,517 was developed by Spectral Diagnostics (SD) Ltd., Industrial Park, Migdal Haemek, Israel and will be referred hereinbelow as SpectraCube™. The SpectraCube™ system optically connected to a variety of optical devices was used to implement the method of the present invention. The SpectraCube™ system has the following characteristics, listed hereinbelow in Table 1:

TABLE 1

| Character | Performance |
| --- | --- |
| Spatial resolution: | 30/M μm (M = effective microscope or fore optics magnification) |
| Field of View: | 8/M millimeter |
| Sensitivity: | 20 milliLux (for 100 msec integration time, increases for longer integration times linearly with $\sqrt{T}$ |
| Spectral range: | 400–1000 nm |
| Spectral resolution: | 4 nm at 400 nm (16 nm at 800 nm) |
| Acquisition time: | 5–50 sec, typical 25 sec |
| FFT processing time: | 20–180 sec, typical 60 sec |

DISPLAY AND ANALYSIS OF SPECTRAL IMAGES a. General

As mentioned above, a spectral image is a three dimensional array of data, I(x,y,λ), that combines spectral information with spatial organization of the image. As such, a spectral image is a set of data called a spectral cube, due to its dimensionality, which enables the extraction of features and the evaluation of quantities that are difficult, and in some cases even impossible, to obtain otherwise. Since both spectroscopy and digital image analysis are well known fields that are covered by an enormous amount of literature [see, for example, Jain (1989) Fundamentals of Digital Image Processing, Prentice-Hall International], the following discussion will focus primarily on the benefit of combining spectroscopic and imaging information in a single data set i.e., a spectral cube.

One possible type of analysis of a spectral cube is to use spectral and spatial data separately, i.e., to apply spectral algorithms to the spectral data and two-dimensional image processing algorithms to the spatial data.

As an example of a spectral algorithm, consider an algorithm computing the similarity between a reference spectrum and the spectra of all pixels (i.e., similarity mapping) resulting in a gray (or other color) scale image (i.e., a similarity map) in which the intensity at each pixel is proportional to the degree of 'similarity'. This gray scale image can then be further analyzed using image processing and computer vision techniques (e.g., image enhancement, pattern recognition, etc.) to extract the desired features and parameters. In other words, similarity mapping involves computing the integral of the absolute value of the difference between the spectrum of each pixel of the spectral image with respect to a reference spectrum (either previously memorized in a library, or belonging to a pixel of the same or other spectral image), and displaying a gray level or pseudocolor (black and white or color) image, in which the bright pixels correspond to a small spectral difference, and dark pixels correspond to a large spectral difference, or vice versa.

Similarly, classification mapping perform the same calculation as described for similarity mapping, yet takes several spectra as reference spectra, and paints each pixel of the displayed image with a different predetermined pseudocolor, according to its classification as being most similar to one of the several reference spectra.

It is also possible to apply spectral image algorithms based on non-separable operations; i.e., algorithms that include both local spectral information and spatial correlation between adjacent pixels (one of these algorithms is, as will be seen below, a principal component analysis).

One of the basic needs that arise naturally when dealing with any three-dimensional (3D) data structure such as a spectral cube (i.e., $I(x,y,\lambda)$), is visualizing that data structure in a meaningful way. Unlike other types of 3D data such as tomographic data, $D(x,y,z)$, obtained for example by a confocal microscope, where each point represents, in general, the intensity at a different locations $(x,y,z)$ in tree-dimensional space, a spectral image is a sequence of images representing the intensity of the same two-dimensional plane (i.e., the sample) at different wavelengths. For this reason, the two most intuitive ways to view a spectral cube of data is to either view the image plane (spatial data) or the intensity of one pixel or a set of pixels as function of wavelength in a three-dimensional mountain-valley display. In general, the image plane can be used for displaying either the intensity measured at any single wavelength or the gray scale image that results after applying a spectral analysis algorithm, over a desired spectral region, at every image pixel. The spectral axis can, in general, be used to present the resultant spectrum of some spatial operation performed in the vicinity of any desired pixel (e.g., averaging the spectrum).

It is possible, for example, to display the spectral image as a gray scale image, similar to the image that might be obtained from a simple monochrome camera, or as a multicolor image utilizing one or several artificial colors to highlight and map important features. Since such a camera simply integrates the optical signal over the spectral range (e.g., 400 nm to 760 nm) of the CCD array, the 'equivalent' monochrome CCD camera image can be computed from the 3D spectral image data base by integrating along the spectral axis, as follows:

$$\text{gray\_scale}(x, y) = \int_{\lambda 1}^{\lambda 2} w(\lambda) \cdot I(x, y, \lambda) d\lambda \quad (3)$$

Figure 4:
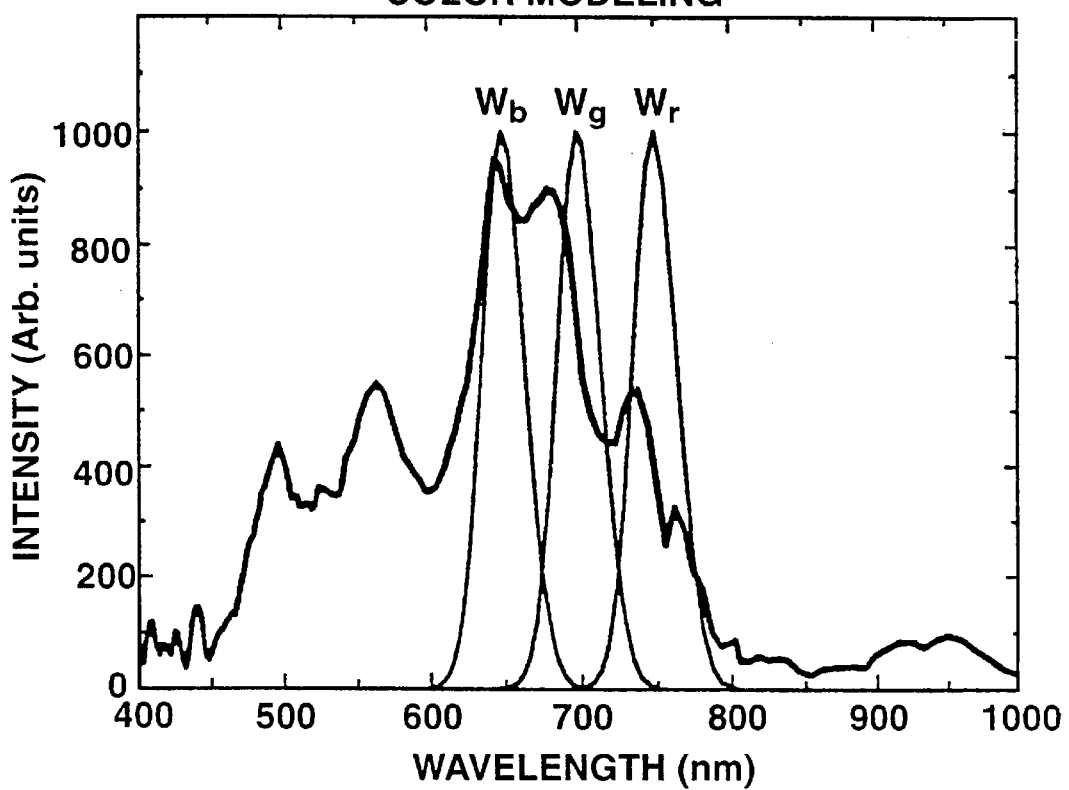
FIG. 4 shows a definition of pseudo-RGB (Red, Green and Blue) colors for emphasizing chosen spectral ranges. The intensity for each pseudo-color is calculated by integrating the area under the curve, after multiplying it by one of the curves.
Figure 5:
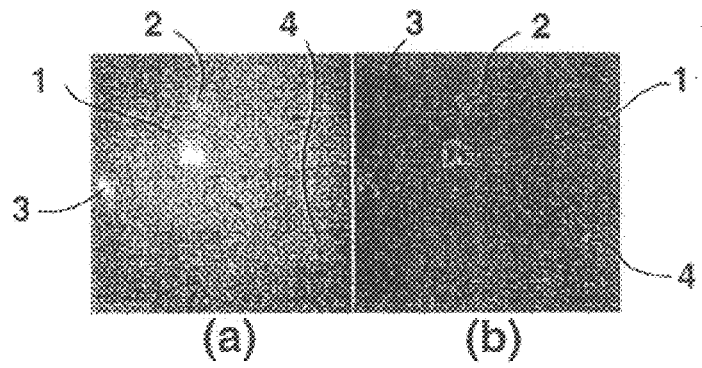
FIGS. 5a, 5b and 5c show interphase FISH performed with two different probes attached to Texas-Red and Rhodamine wherein (a) is an original image, the way it looks thorough a microscope; (b) is the same sample, after being measured and processed by the method of the present invention; and (c) are the fluorescence spectra of the Texas-Red and Rhodamine fluorophores.
Figure 5:
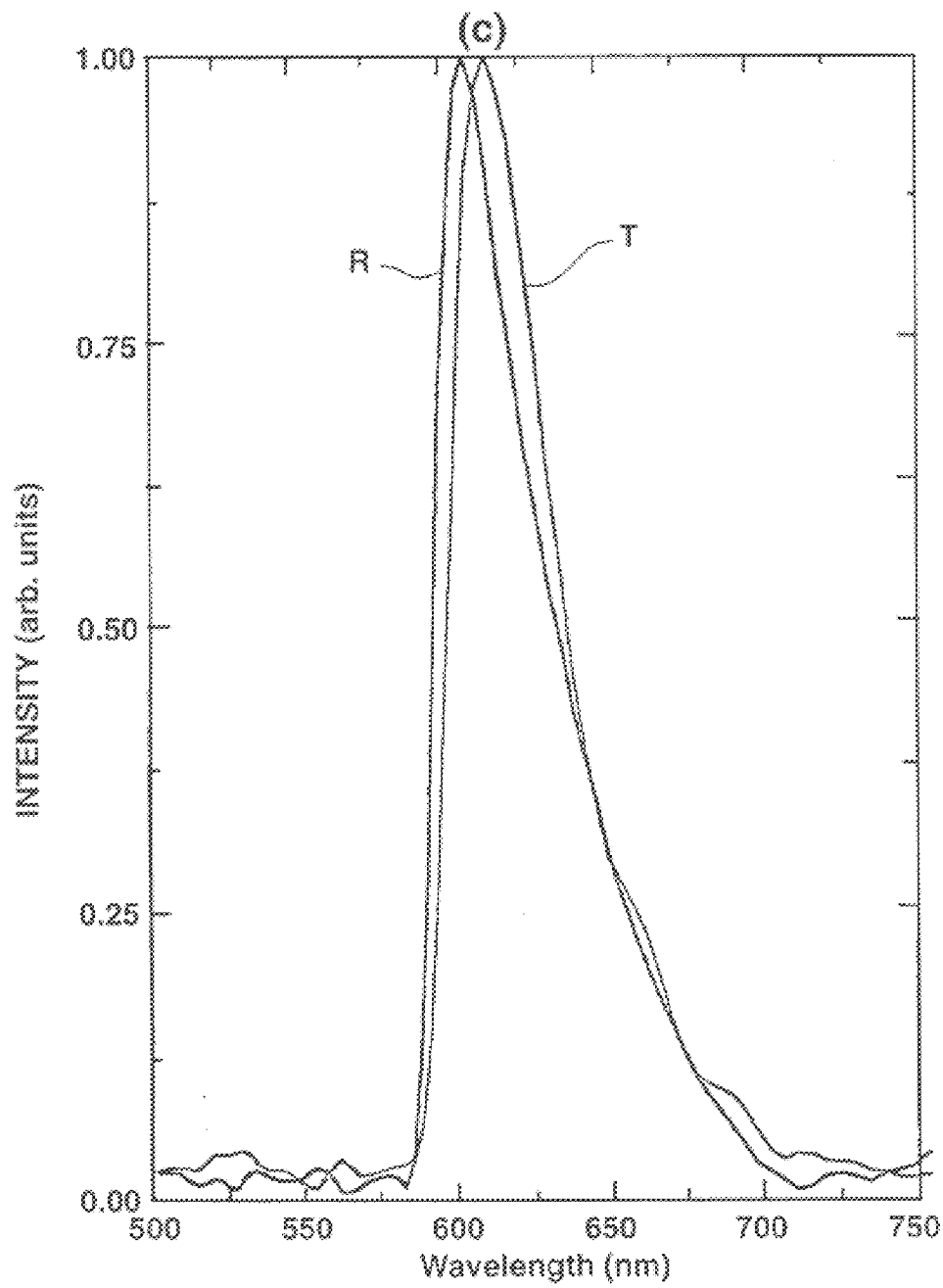

In equation 3, $w(\lambda)$ is a general weighting response function that provides maximum flexibility in computing a variety of gray scale images, all based on the integration of an appropriately weighted spectral image over some spectral range. For example, by evaluating equation (3) with three different weighting functions, $\{w_r(\lambda), w_g(\lambda), W_b(\lambda)\}$, corresponding to the tristimulus response functions for red (R), green (G) and blue (B), respectively, it is possible to display a conventional RGB color image. It is also possible to display meaningfull non-conventional (pseudo) color images. FIG. 4 presents an example of the power of this simple algorithm. Consider choosing $\{w_r, w_g, W_b\}$ to be Gaussian functions distributed "inside" a spectrum of interest, the resulting pseudo-color image that is displayed in this case emphasizes only data in the spectral regions corresponding to the weighting functions, enabling spectral differences in these three regions to be detected more clearly.

b. Point operations

Point operations are defined as those that are performed on single pixels, (i.e., do not involve more than one pixel at a time). For example, in a gray scale image, a point operation can be one that maps the intensity of each pixel (intensity function) into another intensity according to a predetermined transformation function. A particular case of this type of transformation is the multiplication of the intensity of each pixel by a constant.

The concept of point operations can also be extended to spectral images: here each pixel has its own intensity function (spectrum), i.e., an n-dimensional vector $V_1(\lambda)$; $\lambda\epsilon[\lambda_1, \lambda_n]$. A point operation applied to a spectral image can be defined as one that maps the spectrum of each pixel into a scalar (i.e., an intensity value) according to a transformation function:

$$v_2 = g(V_1(\lambda)); \lambda\epsilon[\lambda_1, \lambda_n] \quad (4)$$

Building a gray scale image according to Equation 4 is an example of this type of point operation. In the more general case, a point operation maps the spectrum (vector) of each pixel into another vector according to a transformation function:

$$V_2(l) = g(V_1(\lambda)); l\epsilon[l, N], \lambda\epsilon[\lambda_1, \lambda_n,] \quad (5),$$

where $N \leq n$.

In this case a spectral image is transformed into another spectral image.

One can now extend the definition of point operations to include operations between corresponding pixels of different spectral images. An important example of this type of algorithm is optical density analysis. Optical density is employed to highlight and graphically represent regions of an object being studied spectroscopically with higher dynamic range than the transmission spectrum. The optical density is related to transmission by a logarithmic operation and is therefore always a positive function. The relation between the optical density and the measured spectra is given by Lambert Beer law:

$$OD(\lambda) = -\log_{10}\frac{I(\lambda)}{I_0(\lambda)} = -\log_{10}\tau(\lambda) \quad (6)$$

where $OD(\lambda)$ is the optical density as a function of wavelength, $I(\lambda)$ is the measured spectrum, $I_0(\lambda)$ is a measured reference spectrum, and $\tau(\lambda)$ is the spectral transmitance of the sample. Equation 6 is calculated for every pixel for every wavelength where $I_0(\lambda)$ is selected from (1) a pixel in the same spectral cube for which OD is calculated; (2) a corresponding pixel in a second cube; and (3) a spectrum from a library.

Note that the optical density does not depend on either the spectral response of the measuring system or the non-uniformity of the CCD detector. This algorithm is useful to map the relative concentration, and in some cases the absolute concentration of absorbers in a sample, when their absorption coefficients and the sample thickness are known. It should thus be noted that the term 'level' as used herein also refers to the terms 'amount', 'relative amount', 'absolute concentration' and 'relative concentration'.

Additional examples include various linear combination analyses, such as for example: (1) applying a given spectrum to the spectrum of each of the pixels in a spectral image by an arithmetical function such as addition, subtraction, multiplication division and combinations thereof to yield a new spectral cube, in which the resulting spectrum of each pixel is the sum, difference, product ratio or combination between each spectrum of the first cube and the selected spectrum; and (2) applying a given scalar to the spectra of each of the pixels of the spectral image by an arithmetical function as described above.

Such linear combinations may be used, for example, for background subtraction in which a spectrum of a pixel located in the background region is subtracted from the spectrum of each of the pixels; and for a calibration procedure in which a spectrum measured prior to sample analysis is used to divide the spectrum of each of the pixels in the spectral image.

Another example includes a ratio image computation and display as a gray level image. This algorithm computes the ratio between the intensities at two different wavelengths for every pixel of the spectral image and paints each of the pixels in a lighter or darker artificial color accordingly. For example, it paints the pixel bright for high ratio, and dark for low ratio (or the opposite), to display distributions of spectrally sensitive materials.

c. Spatial-spectral combined operations

In all of the spectral image analysis methods mentioned above, algorithms are applied to the spectral data. The importance of displaying the spectrally processed data as an image is mostly qualitative, providing the user with a useful image. It is also possible, however, depending on the application, to use the available imaging data in even more meaningful ways by applying algorithms that utilize the spatial-spectral correlation that is inherent in a spectral image. Spatial-spectral operations represent the most powerful types of spectral image analysis algorithms. As an example, consider the following situation:

A sample contains k cell types stained with k different fluorophores (the term 'cell' here is used both for a biological cell, and also as 'a region in the field of view of the instrument'). Each fluorophore has a distinct fluorescence emission spectrum and binds to only one of the k cell types. It is important to find the average fluorescence intensity per cell for each one of the k cell types. To achieve this task the following procedure can be used: (1) classify each pixel in the image as belonging to one of k+1 classes (k cell types plus a background) according to its spectrum; (2) segment the image into the various cell types and count the number of cells from each type; and (3) sum the fluorescence energy contributed by each class, and divide it by the total number of cells from the corresponding class.

This procedure makes use of both spectral and spatial data. The relevant spectral data takes the form of characteristic cell spectra (i.e., spectral "signatures"), while the spatial data consists of data about various types of cells (i.e., cell blobs) many of which appear similar to the eye. The ideal type of measurement for this type of situation is a spectral image. In the above situation, cells can be differentiated by their characteristic spectral signature. Hence, a suitable point operation will be performed to generate a synthetic image in which each pixel is assigned one of k+1 values. Assuming that the fluorescence emission spectra of the different cell types are known to be $s_i(\lambda)$; i=1, 2, ..., k, $\lambda \in [\lambda_1, \lambda_n]$, and the measured spectrum at each pixel (x, y) is $s_{xy}(\lambda)$ $\lambda \in [\lambda_1, \lambda_n]$, then the following algorithm is a possible method of classification (step 1 above):

Let $e^2_i$ be the deviation of the measured spectrum from the known spectrum of the fluorophore attached to cell type i. Then, adopting a least-squares "distance" definition, one can write:

$$e_i^2 = \sum_{\lambda \in R_\lambda} (s(\lambda) - s_i(\lambda))^2 \quad (7)$$

where $R_\lambda$ is the spectral region of interest. Each point [pixel (x, y)] in the image can then be classified into one of the k+1 classes using the following criterion:

point(x,y)∈ class k+1 if $e^2_i$>threshold for all $i \in [l,k]$, whereas
point(x,y)∈ class ρ if $e^2_i$<threshold, and ρ is such that min[$e^2_i$]= $e^2_\rho$ (8)

Steps 2 and 3 above (image segmentation and calculation of average fluorescence intensity) are now straight-forward using standard computer vision operations on the synthetic image created in accordance with the algorithm described in equations 7 and 8.

Another approach is to express the measured spectrum $s_{x,y}(\lambda)$ at each pixel as a linear combination of the k known fluorescence spectra $s_i(\lambda)$; i=1, 2, ..., k. In this case one would find the coefficient vector C=[$c_1, c_2, \ldots, c_k$] that solves:

$$F = \min \sum_{\lambda \in R_\lambda} (s(\lambda) - \hat{s}(\lambda))^2 \quad (9)$$

where $\hat{s}(\lambda) = \sum_{i=1}^{k} c_i \cdot s_i(\lambda)$,

Solving for $$\frac{dF}{dc_i} = 0;$$

for i=1,2, ..., k(i.e., find values of $c_i$ which minimize F) yields the matrix equation C A B (10), where A is a square matrix of dimension k with elements $$a_{m,n} = \left[ \sum_{\lambda \in R_\lambda} s_m(\lambda) \cdot s_n(\lambda) \right], \quad (11)$$

and B is a vector defined as $$b_m = \left[ \sum_{\lambda \in R_\lambda} s_m(\lambda) \cdot s(\lambda) \right], \quad m, n = 1, 2, ..., k. \quad (12)$$

Arithmetic operations may similarly be applied to two or more spectral cubes and/or spectra of given pixels or from a library. For example consider applying an arithmetic operations between corresponding wavelengths of corresponding pairs of pixels belonging to a first spectral cube of data and a second spectral cube of data to obtain a resulting third spectral cube of data for the purpose of, for example, averaging two spectral cubes of data, time changes follow-up, spectral normalization, etc.

In many cases objects (e.g., cells) present in a spectral image differ from one another in chemical constituents and/or structure to some degree. Using a principal component analysis by producing covariance or correlation matrix enhances these small differences. A brief description of the principal component analysis using a covariance matrice is given below. For further details regarding the principal component analysis, the reader is referred to Martens and Naes (1989) Multivariate Calibration, John Wiley & Sons, Great Britain; and to Esbensen et al., Eds. (1994) Multi variance analysis—in practice. Computer-aided modeling as CAMO, and the Unscrambler's User's guide, Trondheim, Norway.

Thus, the intensities of the pixels of the image at wavelength $\lambda_i$(i=1, ... N) are now considered a vector whose length is equal to the number of pixels q. Since there are N of these vectors, one for every wavelength of the measurement, these vectors can be arranged in a matrix B' with q rows, and N columns:

$$B' = \text{No. of pixels} \begin{pmatrix} B'_{11} & \cdots & B'_{1N} \\ \vdots & & \vdots \\ B'_{q1} & \cdots & B'_{qN} \end{pmatrix} \quad \text{No. of wavelengths} \quad (13)$$

For each of the columns of matrix B' defined is an average:

$$M_i = \frac{1}{q}\sum_{i=1}^{q} B'_{ji}; i = 1 \ldots N \quad (14)$$

and a second normalized matrix B defined as:

$$B = \text{No. of pixels} \begin{pmatrix} \frac{B'_{11}}{M_1} & \cdots & \frac{B'_{1N}}{M_N} \\ \vdots & & \vdots \\ \frac{B'_{q1}}{M_1} & \cdots & \frac{B'_{qN}}{M_N} \end{pmatrix} \quad \text{No. of wavelengths} \quad (15)$$

A covariance matrix C is defined for the matrix B: $C = B^T \cdot B$ of dimensions N×N. C is diagonalized, and eigenvectors and eigenvalues related by: $C V_i = \mu_i \cdot V_i$ where Vi are N orthogonal unit vectors and $\mu_i$ are the eigenvalues representing the variance in the direction of the i-th unit vector $V_i$. In general, the lowest components represent the highest variability as a function of pixels.

The products $BV_i$(i=1, ... N) are the projections of the spectral image onto the elements of the orthogonal basis, They are vectors with q elements (q=number of pixels), and can be displayed separately as black and white images. These images may reveal features not obvious from a regular black and white image filtered at a certain wavelength or wavelength range.

FLUORESCENCE MICROSCOPY a. General

The use of multiple dyes (i.e., fluorophores) [see, Jain (1989) Fundamentals of Digital Image Processing, Prentice-Hall International], is one of the most powerful and common tools for analyzing tissues and cells. Fluorescence microscopy is therefore one of the most important experimental methods used in light microscopy [Lakowicz (1983) Principles of fluorescence spectroscopy, Plenum Press, New York, London]. The power of fluorescent probes is mainly due to the great variety of biological structures to which specific dyes can be bound [Waggoner (1986) Applications of fluorescence in the biomedical sciences, Eds. Taylor et al., New York: Alan R. Liss, Inc. pp. 3–28]. For a detailed review of fluorescent probes see, Mason (editor) (1993) Fluorescent and Luminescent Probes for Biological Activity, Biological Techniques Series, edited by Sattelle, Academic Press Limited, London; and, Ploem and Tanke (1987) Introduction to Fluorescence Microscopy, Oxford University Press, Royal Microscopical Society.

The rapid development of new and more sophisticated multicolor fluorescent dye molecules will continue to create a need for more advanced fluorescence imaging techniques that can utilize the full potential of these dyes. For a discussion of the revolutionary impact fluorescent dyes have had, and will continue to have, on the way research is conducted today, refer to Taylor et al. (1992) The New Vision of Light Microscopy, American Scientist, Vol. 80, pp. 322–335.

A remarked improvement in multicolor fluorescent dyes is the introduction of combinatorial fluorescent dyes which are various combinations of few basic fluorescent dyes, see, Ried et al., (1992) Simultaneous visualization of seven different DNA probes by in situ hybridization using combinatorial fluorescence and digital imaging microscopy. Proc. Natl. Acad. Sci. U.S.A. 89, 1388–1392; and, Ried (January 1994) Fluoreszenz in situ Hybridizierung in der genetischen Diagnostik, Faculty of theoretical medicine, Ruprecht-Karls University Heidelberg.

Spectral bio-imaging using the method of the present invention, provides several important advantages for fluorescence imaging applications over simple filter based approaches. These advantages include the following: (1) measurement of the complete spectrum, providing much more quantitative insight into the actual behavior of dye molecules in the sample of interest; (2) ability to overcome many of the traditional problems arising from undesirable background luminescence; (3) undesirable or unpredictable spectral shifts that occur in the emission spectrum of a fluorescent probe, due to its micro-environment (e.g., temperature), can be taken into account in determining the probe concentration, whereas when the fluorescence intensity is only measured with a band-pass filter, such spectral shifts would not only go undetected but might cause significant errors in analyzing the probe concentration; and, (4) simplification of fluorescence image acquisition and, as will be shown below in detail, when used in conjunction with the appropriate spectral analysis algorithms it is possible to separate and map, in a single measurement, many spectrally overlapping fluorescent dyes. In fact, by applying sophisticated data analysis algorithms such as multivariate analysis, principal component regression and other classification algorithms [see, Martens and Naes (1989) Multivariate Calibration, John Wiley & Sons, Great Britain] it is possible to analyze many spectrally related parameters simultaneously.

Spectral bio-imaging according to the present invention provides means for eliminating problems associated with undesirable background luminescence as follows. Fluorescence imaging microscopy is typically performed by using a fluorescence filter cube which ensures that the sample is excited by the desired short wavelengths, and that only wavelengths in a limited spectral band corresponding to the fluorescence emission of the probe reach the detector (e.g., eye, camera, etc.) [Mason (editor) (1993) Fluorescent and Luminescent Probes for Biological Activity, Biological Techniques Series, edited by Sattelle, Academic Press Limited, London]. Since fluorescence intensities are usually several orders of magnitude below the intensity of the excitation source, such background luminescence can never be eliminated perfectly [Benson et al. (1985) Cell Biol. 100, pp. 1309–1323]. The three primary sources for undesirable background luminescence are: (1) radiation from the excitation source that is not completely blocked by the dichroic mirror coating and/or the filter; (2) auto-fluorescence of the sample, and sometimes also from the optical elements; and (3) selection of an inappropriate (or sub-optimal) combination of excitation filter, dichroic mirror and barrier filters. These sources can contribute significantly to the background fluorescence. The effects of sample auto-fluorescence can usually be reduced by selecting fluorescent probes whose absorption and emission bands do not overlap with those of the sample being measured. Similarly, by choosing optical elements that are appropriately coated to reduce auto-fluorescence, the effects of this type of auto-fluorescence can also be minimized.

In spite of the best filtering methods available, undesirable background luminescence makes it often difficult, and sometimes impossible, to bring out the relevant fluorescence signal from its background (noise). The spectral bio-imaging method of the present invention is able, on the other hand, to use spectral differences between (i) the spectral shape and spectral range of the fluorescent dye and (ii) the spectral shape and spectral range of the background luminescence (including auto-fluorescence), to eliminate the effects of undesirable background luminescence.

Thus, by applying the appropriate spectral image analysis methods to the emission spectra of fluorescent probes, it is possible to improve the signal-to-noise ratio, and hence the accuracy, of fluorescence imaging measurements. This advantage of the spectral bio-imaging approach is of particular importance for ratio imaging, when quantitation of the results is desired. In addition, the spectral bio-imaging system of the present invention can save time and effort that is otherwise spent in choosing the optimal filters for a filter based measurement.

The acquisition of multicolor fluorescence images can be greatly simplified is when the power of spectral bio-imaging according to the method of the present invention, is combined with the appropriate fluorescent markers. In order to fully realize the benefits afforded by spectral bio-imaging, the reader is asked to consider the typical steps involved in using a filter based imaging method to measure the fluorescence from a sample containing multiple probes. First, probes with sufficiently different absorption and emission spectra must be selected. In todays practice, this requirement limits the number of fluorescent markers in a specimen to between three and five probes. Fluorescence images are then acquired, one image for each dye, by appropriately rotating two filter wheels, one for selecting the excitation wavelength and another for capturing the emission spectrum, or alternatively, rotating one filter wheel aimed at selecting the excitation wavelength, while capturing the emission spectrum is by a triple dichroic filter. Approaches in which tunable filters (no moving parts) are used to control the excitation and/or emission wavelength have also been proposed. Recently, multispectral interference filters have also been used to enable imaging multiple fluorophores [Lengauer et al. (1993) Human Molecular Genetics 2, pp. 505–512]. Means of changing the dichroic mirror (e.g., by changing filter cubes) is also required. It is also frequently necessary to readjust the focus of the image at each wavelength and sometimes even the CCD camera exposure time must be changed to achieve higher signal-to-noise ratios. Collectively, these limitations create a registration problem.

The resulting monochrome images, each corresponding to the emission of a different fluorescent dye, are then pseudo-colored and superimposed (using a digital computer with readily available off-the-shelf software). The resulting image shows the location of several fluorescent markers, each colored with a different pseudo-color. Since slight changes in the position of the dichroic mirror will cause translational shifts in the digitized images, it is necessary to use multiple wavelength dichroic mirrors [for use of a dichroic with quadruple wavelength band-pass properties see, Hiraoka et al. (1992) Seminars in Cell Biology, Vol. 2, pp. 153–164] or to register the images prior to their superposition. The image registration approach is more common, despite the fact that image registration is a difficult problem which can be time consuming and often produces only marginally satisfactory results. These are technical challenges which must also be addressed when acquiring multicolor fluorescence images [Waggoner et al. (1989) Part B of Methods in Cell Biology, Vol. 30, Ch. 17, pp. 449–478, edited by Taylor and Wang, Academic Press Inc.].

The spectral bio-imaging method of the present invention thus overcome one of the fundamental limitations imposed by filter based approaches to fluorescence imaging. By enabling the simultaneous measurement of the emission spectrum of an unlimited number of fluorescent dyes (including dyes whose emission spectra overlap to a great extent, as demonstrated hereinbelow in the Examples section for the Texas-Red and Rhodamine fluorophores), spectral bio-imaging eliminates the need for sequentially acquiring images of the emissions of multiple fluorescent probes. The advantage of using a spectral bio-imaging system is greatest when the used fluorescent probes can be excited by a common excitation source. In this case, a single spectral image acquisition can capture the fluorescence emission of an almost unlimited number of dyes and the need to (1) select non-overlapping dyes; (2) change filter cubes; (3) change excitation or emission filters; (4) optimize the focus and/or exposure time or (5) register the images, is eliminated. The challenge, of course, is to select suitable dyes that can be excited with a common source. Dyes which are excited by fluorescence energy that is transferred to/from one another are thus ideally suited for multi-color fluorescence imaging using a spectral bio-imaging system. Clearly, the use of dyes with similar emission properties will make visual detection (e.g., under the microscope) more difficult; however, this limitation is likely to be solved using the spectral bio-imaging method of the present invention.

b. Spectral identification of multiple fluorophores

The use of the spectral bio-imaging method according to the present invention enables the simultaneous measurement of many dyes (i.e., fluorophores, fluorescent moieties) in one measurement. There is no restriction on the type of dye, even dyes that overlap spectrally (e.g., Rhodamine and Texas-Red) can be identified as will be exemplified below (see, Example 1 and 2) by applying suitable algorithms (e.g., linear combination for background subtraction, etc.) and their occurrence mapped in an image. However, if many dyes are to be used simultaneously, careful consideration should be given to their excitation wavelengths, fluorescence intensities and emission spectra. When this is done properly, the results can be analyzed quantitatively as well. For example, the relative concentration of several proteins can be mapped in a single measurement using suitable fluorescently tagged antibodies which specifically bind to these proteins. By using standard calibrated dyes, the absolute concentrations can also be determined.

One important example where the detection of multiple fluorescent probes can be a significant advantage is FISH (fluorescent in situ hybridization) [Emanuel (1993) Growth Genetics and Hormones 9, pp. 6–12], which is used to analyze genes at the chromosome level, and find possible genetic defects such as gene/chromosome amplification, deletion, translocation, rearrangement and other abnormalities.

Certain diseases and disorders, including many cancers and birth defects, are genetic disorders caused by defects in one or more genes. Many other diseases are known or believed to have a genetic component(s), that is, there exists genetic defect(s) that does not alone cause the disease but contributes to it, or increases the probability of developing the disease later in life, phenomena known in the art as multifactorial diseases and genetic predispositions. Correlation of visible genetic defects with known diseases would allow doctors to make definitive diagnoses, and permit early detection and treatment of many diseases. Genetic counseling could alert prospective parents and at-risk individuals to the possibility of potentially serious medical problems in the future, permitting appropriate intervention.

More than 5,000 genetic disorders have now been identified, many of which are associated with multiple genetic defects. After the discovery that chromosomes are the carriers of hereditary information, scientists reasoned that it should be possible to document visible defects in chromosomes that were responsible for specific disorders. In the 1960's, staining techniques were developed for microscopy-based classification of metaphase chromosomes spread onto glass slides. For several decades, visual analysis of chromosomes banding patterns has been used to correlate human genetic disorders with observed structural abnormalities in metaphase chromosomes. Chromosomes are typically examined by brightfield microscopy after Giemsa staining (G-banding), or examined by fluorescence microscopy after fluorescence staining (R-banding), to reveal characteristic light and dark bands along their length. Careful comparison of a patient's banding pattern with those of normal chromosomes can reveal abnormalities such as translocations (exchange of genetic material between or within chromosomes), deletions (missing chromosomes or fragments of chromosomes), additions, inversions and other defects that cause deformities and genetic diseases.

However, many serious genetic diseases, such as for example cystic fibrosis (CF) and many others, are caused by mutations that involve addition, deletion or substitution of only one or a few nucleotides. Such small defects are not detectable by the chromosomal banding techniques described above, and for many years cytogeneticists have been working to develop techniques for locating and quantifying minute defects.

Fluorescent in situ hybridization (FISH) has evolved over the past 25 years through the improvement of a number of complementary techniques. Its emergence has been driven by the desire of cytogeneticists to develop better tools for mapping the precise location of genes on chromosomes, and to detect very small genetic defects not visible by gross staining of chromosomes. The human genome project (HGP), a bold initiative to identify and map all human genes, has identified interest in FISH and has hastened the development of much-needed DNA probes. Current FISH techniques have also been made possible by the concurrent development of powerful immunological probes, a growing variety of excellent fluorescent dyes for microscopy and spectroscopy, and dramatic improvements in the objectives, illuminators and filters used for fluorescence microscopy.

The power and utility of FISH is due to many factors: (1) FISH can be used not only on isolated chromosomes and nuclei, but also whole cells within fixed, paraffin-embedded tissue sections; (2) it can detect relatively small defects (ability of detecting smaller defects being constantly increased); (3) it can provide results relatively quickly; (4) its moderate cost allows it to be used in most diagnostic and research laboratories; (5) adaptation can be developed for various probes and specimen types; and, (6) high specificity and sensitivity can be achieved (7) within a short throughput, typically two hours.

Many FISH applications require only that the cytogeneticist look through the eyepieces of a microscope, or at the image on the monitor, to determine whether a fluorescent label is present or absent. With somewhat more complex specimens, a simple count of one or two colored labels may be done. However, the ability to process digital images and extract numerical data from them adds a vast new set of capabilities to FISH techniques. An appropriate imaging method, such as the method of the present invention, can enhance very faint FISH images so that labeled chromosomes and loci are clearly identifiable. Under readily achieved experimental conditions, the number of labeled sites can be automatically counted. In addition, the intensity at each labeled site can be measured and the amount of DNA calculated to reveal, for example, the number of copies present of a particular gene. Emerging techniques such as multicolor FISH employ color image analysis to detect and quantify multiple (3,4,5 and more) fluorescent probes.

As discussed above, FISH can provide information on the location of the labeled probe, the number of labeled sites on each chromosome, and the intensity of labeling (the amount of genetic material) at each site. Centromeric (repetitive DNA) probes and chromosome paints are used to tag and count the number of copies present of each targeted chromosomes. Locus-specific probes are used to map the location of small regions of genetic material. These types of probes can be used on intact interphase nuclei as well as metaphase chromosome spreads, and can be counted visually or automatically by a suitable algorithm. They are routinely used to identify genetic diseases characterized by having too many or too few copies of a specific chromosome, chromosome fragment, or gene.

In very early stages of some cancers, long before the cells are recognizably abnormal, there may be an increase in the number of specific genes, phenomenon known in the art as gene amplification, that are detectable using locus-specific probes. Using FISH to detect chromosome abnormalities in cancerous cells may point out the developmental stage the disease have reached and therefore to select the most suitable treatment(s), many of which are stage specific in their effectiveness. Thereby precious time is saved and patients suffering is minimized, selecting the most effective stage specific treatment.

It is possible to uniformly label the entire surface of one specific chromosome by isolating the chromosome (using flow cytometry, for example), physically (e.g., by sonication) or enzymatically (e.g., by endonucleases) chopping it up, and generating a set of probes against all of the fragments. Whole chromosome probes, also known as chromosome paints, will fluorescently label all copies of the target chromosome. One important application of chromosome painting is the detection of deletions and translocations between two chromosomes, as characteristically occurs in early stages of certain cancers.

For example, if chromosome A is specifically labeled with a green paint and chromosome B is labeled with a red paint, any translocation of material from A to B will appear as a green area on a red chromosome (and vice versa). Typically, chromosome paints generated from normal chromosomes are used to detect deletions or translocations on abnormal (patient) chromosomes. Reverse chromosome painting uses probes generated from an abnormal chromosome to identify DNA from various normal chromosomes which contributed material to the abnormal chromosome. The method of the present invention, as exemplified hereinbelow in the Examples section, enables to paint the 24 different chromosomes comprising the human karyotype (i.e., genome) each in a different color and simultaneously detect, identify and meaningfully display a color human karyotype, using a single hybridization followed by a single measurement.

Comparative genomic hybridization (CGH) is a variation of reverse chromosome painting in which two cocktails of DNA probes are generated from entire sets of chromosomes. One cocktail is generated from a set of normal chromosomes, and another from a set of abnormal (e.g., tumor) chromosomes. The two sets of probes are generated using different reporter molecules so that, for example, normal DNA will exhibit red fluorescence, and abnormal DNA will exhibit green fluorescence. A normal metaphase spread is hybridized simultaneously with both cocktails, and currently evaluated using color image analysis. Regions of normal chromosomes that fluoresce more intensely green than red indicate that DNA amplification (multiple gene copies) has occurred at that gene in the patient's abnormal cells. Regions with more red than green fluorescence (decreased green/red ratio) indicate sites of genetic deletions in the patient's chromosomes, and regions with equal green and red fluorescence indicate that no DNA changes have occurred at that site. CGH and related techniques are more complex than previous labeling techniques, yet they offer the ability to detect and quantify more subtle and extensive genetic alterations than were previously possible. The method of the present invention is highly suitable for these types of analyses.

From what has been said above, it follows that karyotyping, translocation/rearrangement detection, chromosome deletion/amplification, and gene mapping will greatly benefit by the use of the sensitive, quantitative, spectral imaging method of the present invention that builds a whole spectral image at relatively high spectral resolution, instead of a simple color fluorescence image. This is because such method will decrease the sample preparation time and will be able to distinguish between a hybridized fluorescent probe from one that is residual in the background (by small spectral shifts), and will be able to measure a yet not achieved large number of probes, simultaneously.

Thus one of the objectives of the present invention is to provide a FISH imaging method designed to exploit the advances in probe technology. According to the present invention there is a possibility of greatly increasing the number of probes that can be analyzed in any given chromosome analysis, as well as dramatically increasing the speed and degree of automatization at which this information can be acquired as compared with prior art methods.

The FISH imaging method of the present invention exploit the advantages of the SpectraCube™ system, that is capable of simultaneously acquire fluorescence spectra from all pixels of the microscope field of view and detect the location of many fluorescent probes in a single experiment. In conjunction with the availability of chromosome specific probes and novel labeling strategies, and as is exemplified in the Examples below, the method being capable of creating a FISH karyotype with each chromosome being painted with a different color (i.e., 24 different colors for a human karyotype). This method result in extremely high sample throughput and allow analysis of essentially unlimited number of probes.

As delineated above, the key concepts of the present invention is the use of many fluorescent probes in FISH assays. Numerous methods are available to label DNA probes for use in FISH, including indirect methods whereby a hapten such as biotin or digoxigenin is incorporated into DNA using enzymatic reactions. Following hybridization to a metaphase chromosome spread or interphase nuclei a fluorescent label is attached to the hybrid through the use of immunological methods. More recently, fluorescent dyes have been directly incorporated into probes and detected without the use of an intermediate step. Standard FISH dyes include fluorescein, rhodamine, Texas-Red and cascade blue, and multiprobe FISH analysis can be accomplished by labeling different probes with different haptens or fluorescent dyes and combinations thereof, known in the art as combinatorial probes [see, Ried et al., (1992) Simultaneous visualization of seven different DNA probes by in situ hybridization using combinatorial fluorescence and digital imaging microscopy. Proc. Natl. Acad. Sci. U.S.A. 89, 1388–1392; and, Ried (January 1994) Fluoreszenz in situ Hybridizierung in der genetischen Diagnostik, Faculty of theoretical medicine, Ruprecht-Karls University Heidelberg].

Fluorescence is a form of luminescence which occurs after photons of light are absorbed by a molecule known as a fluorophore at the ground electronic state. The molecule is raised to an excited state as a result of electron transfer to a higher energy orbit. This excess energy is dissipated when the electron returns to the original ground state, releasing a quantum of light. The fluorescence light is of longer wavelength than the absorbed light. This shift is limited, causing the emission to be close to the excitation wavelength. Because of this, the fluorophores which can be excited in one spectral range emit in a similar spectral range. For example if the excitation is in the blue range the emission is expected in the green. So if one wants to use many different probes which emit different spectra it is evident that they must be close in wavelength, and also often overlap; as a consequence, spectral resolution is of critical importance to be able to discriminate between the different probes.

According to the method of the present invention, individual probes (a probe as referred to herein in this document also refers to a combinatorial probe) are assigned a pseudo-color (i.e., by an RGB algorithm) or an artificial color (i.e., a predetermined color according to a classification algorithm) and the information is displayed on a computer screen. The use of multicolor fluorescence opens up a possibility of extending FISH into important clinical applications which may benefit from multiple probes. Examples include aneuploidy and chromosome structural studies, detection of marker chromosomes and complete FISH karyotypes. Since multiple information may be gained from a single hybridization, throughput is increased and internal standards may be used in order to assess gene dosage effects or to determine the extent of deletions.

The method of the present invention, utilizes detection of fluorescence excited by a white or coherent monochromatic light source in few narrow spectral bands and a sensor with cooled CCD. Thus, multiple spectra, each representing a different probe, may be simultaneously measured. This, in turn, increases the speed and accuracy of image acquisition, compared to conventional approaches which take multiple snapshots of chromosomes and then reconstruct the image, a process which is time consuming and generates artifactual results, all as described above. Hence, the present invention represents a highly significant progress over the state-of-the-art cytogenetic imaging, because it allows more sensitive, rapid and accurate detection of multiple probes.

Thus, according to the present invention there is provided a fluorescent in situ hybridization method which method includes the steps of (a) providing a cell nuclei having chromosomes, the chromosomes being hybridized with at least one nucleic acid probe, each of the at least one nucleic acid probe including at least one nucleic acid molecule, each of the at least one nucleic acid molecule being labeled with at least one fluorophore; (b) viewing the cell nuclei through a fluorescence microscope, the fluorescence microscope being optically connected to an imaging spectrometer, the fluorescence microscope and the imaging spectrometer being for obtaining a spectrum of each pixel of the cell nuclei by (i) collecting incident light simultaneously from all pixels of the cell nuclei using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the cell nuclei for the entire duration of the measurement and so that the real image of the cell nuclei is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) rotating or translating (i.e., scanning) one or more of the elements of the interferometer system, so that the optical path difference between the two coherent beams generated by the interferometer system is scanned simultaneously for all the pixels of the cell nuclei; and (v) recording signals of each of the detector elements as function of time using a recording device to form a first spectral cube of data; and (c) interpreting the first spectral cube of data using a mathematical algorithm.

The nucleic acid probes may include loci, fragmented chromosomes, yeast artificial chromosomes each including an insert, plasmids, cosmids, phagemids or viral vectors each including an insert, complete (i.e., whole) genomes of a species or a cancerous tissue and combinations thereof. The fluorophores may be single fluorescent dye or a combinatorial fluorescent dye which are various combinations of single fluorescent dyes. The cell nuclei may be a nuclei during interphase, a nuclei during mitosis and a nuclei during meiosis and accordingly the chromosomes may be interphase chromosomes, chromosomes during mitosis or chromosomes during meiosis. The number of nucleic acid probes may be one, two, three, for, five, six, seven, eight, nine, ten, eleven, twelve, thirteen, fourteen, fifteen, sixteen, seventeen, eighteen, nineteen, twenty, twenty one, twenty two, twenty three, twenty four or greater than twenty four, each of the probes include a different fluorophore or a different combination of fluorophores (i.e., a combinatorial probe). The mathematical algorithm may be: (a) a Red-Green-Blue color image computation using predefined wavelength ranges; (b) a classification mapping analysis computing for the spectrum of each of the pixels a spectral difference from at least one reference spectrum; (c) a linear combination analysis, the analysis is for a background subtraction combined with classification mapping analysis; (d) a principal component analysis; and (e) any other algorithm suitable for pixels classification according to their associated spectra.

Reference is now made to the following examples, which together with the above descriptions, illustrate the invention.

EXAMPLE 1

Improved Fluorescent in Situ Hybridization (Fish) using Spectracube™ a Linear Combination Algorithm and a Classification Mapping Algorithm Spectral bio-imaging using the SpectraCube™ system combined with the method of the present invention enhances the usefulness of FISH by allowing the simultaneous detection of a large number of probes, in a single measurement and with high accuracy. As a consequence, the efficiency and the reliability of detection of genetic abnormalities by FISH are greatly increased.

As detailed above, fluorescent in situ hybridization (FISH) plays an increasingly important role in many research and diagnostic areas. Since its first introduction in the 70's the FISH technique has made significant progress, enabling the detection and identification of single gene sequences, partial chromosome sequences and even whole chromosomes (i.e., chromosome painting). The many applications of FISH range from early detection of diseases, to prenatal diagnosis, aneusomy and others, to discover and thereafter treat genetic diseases and abnormalities.

Due to the high sensitivity and selectivity of FISH, which is based on hybridization of homologous nucleic acid sequences, even short sequences as small as 1 kilobase (kb) can be observed (and this will probably improve with time to enable the detection of sequences as short as 15–30 base pairs and, as a consequence, of point mutations). FISH can be applied both to interphase and metaphase cells and even to whole tissues, enabling a broad range of applications both in the fields of cytogenetics and pathology. FISH is improving hand in hand with the improvements of DNA probes, fluorescent dyes (especially the introduction of combinatorial probes), fluorescence microscopy, high performance CCD cameras and imaging techniques.

The ability to detect many probes simultaneously has already been shown in the literature to make FISH an efficient diagnostic tool [Rudkin and Stollar (1977) Nature 55, 172–173]. However, the existing methods are cumbersome and difficult to use. As will be exemplified hereinbelow, the detection of many probes is greatly improved by the SpectraCube TM system combined with appropriate algorithms, because of its spectral resolution and sensitivity. To illustrate this capability, the reader is now referred to FIGS. 5a–c, which include an example of an interphase FISH measurement performed with chromosome 1 and chromosome 17 specific DNA probes tagged with the fluorophores Texas-Red and Rhodamine, respectively, whose fluorescence spectra are very similar. The chromosome 1 probe was a midsatellite probe for the subtelomeric region of the chromosome and was tagged with Texas-Red linked to the DNA probe via biotin post hybridization. The chromosome 17 probe was an a satellite probe for the centromeric region of the chromosome and was tagged with Rhodamine, linked to the second DNA probe via digoxigenin post hybridization. FIG. 5a shows the original image, the way it looks to the eye through the microscope; FIG. 5b shows the same sample, after being measured and processed by the SpectraCube™ system; and, FIG. 5c shows the fluorescence spectra of the Texas-Red (marked as T) and Rhodamine (marked as R) fluorophores.

As seen in FIG. 5c, the spectral peaks of Texas-Red and Rhodamine differ merely by 15 nm, and therefore it would be very difficult to distinguish between them using a filter-based system.

Looking at a color FISH image through a microscope as shown in FIG. 5a, the confidence level of recognizing the correct number of dots (marked 1–4) and of probe types appearing in the image is not particularly high. As shown in FIG. 5b, the SpectraCube™ system, on the other hand, taking advantage of the spectrum measured for each pixel, is able both to verify the existence of the dots, to count them exactly, and to discriminate between the different pairs with a high level of confidence, due to the small spectral difference between them. By artificial coloring of Texas-Red and Rhodamine fluorescence, as shown in FIG. 5c the location of probe specific fluorescence could be determined with high accuracy wherein dots 1 and 2 are of Texas-Red and dots 3 and 4 are of Rhodamine.

FIGS. 6a–b are an example of FISH measurement after hybridization of a nuclear DNA in interphase with six different probes. FIG. 6a shows the original image; FIG. 6b shows the SpectraCube™ measurement, spectral processing and artificial color display of all the detected pairs; and, FIG. 6c the spectra of the six chromophores after hybridization (marked according to the chromosomes each of which labels: 1, 8, 10, 11, 17 and X), as detected through a triple dichroic filter using the SpectraCube™ system. (For details regarding flourophores, probes and chromosomes the reader is referred to the following description, Table 2 below and to Chroma Corp. Cat. No. 61502.

It is apparent from FIG. 6a, showing the original RGB image of the interphasic cell nucleus, that it is difficult to distinguish the colors from one another by eye or even by using a simple RGB color measurement. An experienced observer may, in the best case, detect three different colors of the six. FIG. 6b, however, shows the same sample shown in FIG. 6a, after processing the spectral data with proprietary classification algorithms for background subtraction and classification (see, details above), and the resulting dots have been highlighted with artificial colors as follows: brown—B1; cyan—C; blue—B2; yellow—Y; green—G; and red—R, while the background was given a black—B3, artificial color. As observed, it is possible to see all the six pairs of fluorophores and to easily differentiate among the pairs.

It should be further noted that one pair, the one highlighted in blue (B2), can hardly be noticed by eye, or by using a color camera; however, it is detected after applying a background subtraction algorithm on the spectral cube (compare FIG. 6a with 6b).

The probes used were five α satellite probes for the centromeric regions of chromosomes 8, 10, 11, 17 and X, and a midsatellite probe for the subtelomeric region of chromosome 1. The fluorophores used to label each of the above chromosomes and the DAPI counter stain (backg.), their emission peak and artificial displayed color classification are summarized in Table 2.

Figure 6:
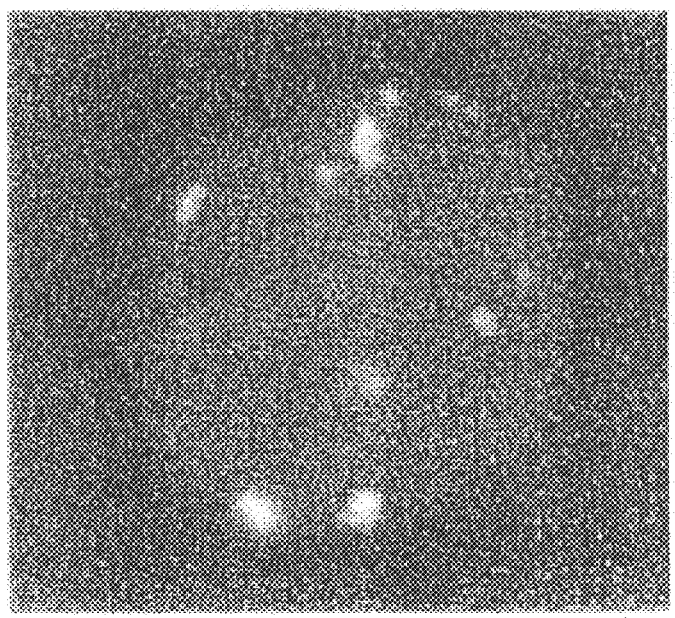
FIGS. 6a, 6b and 6c show interphase FISH performed with six different probes each labeled with a different fluorophore wherein (a) is an original image, the way it looks thorough a microscope, cells were counter stained with DAPI; (b) is the same sample, after being measured and processed by the method of the present invention; and (c) are the fluorescence spectra of the six fluorophores.
Figure 6:
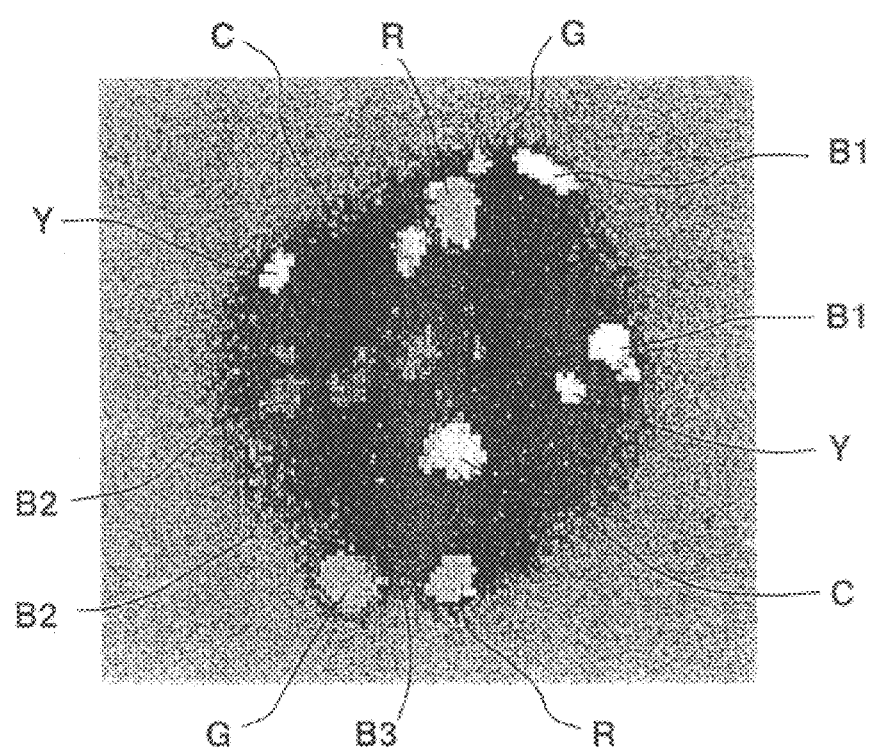
Figure 6C:
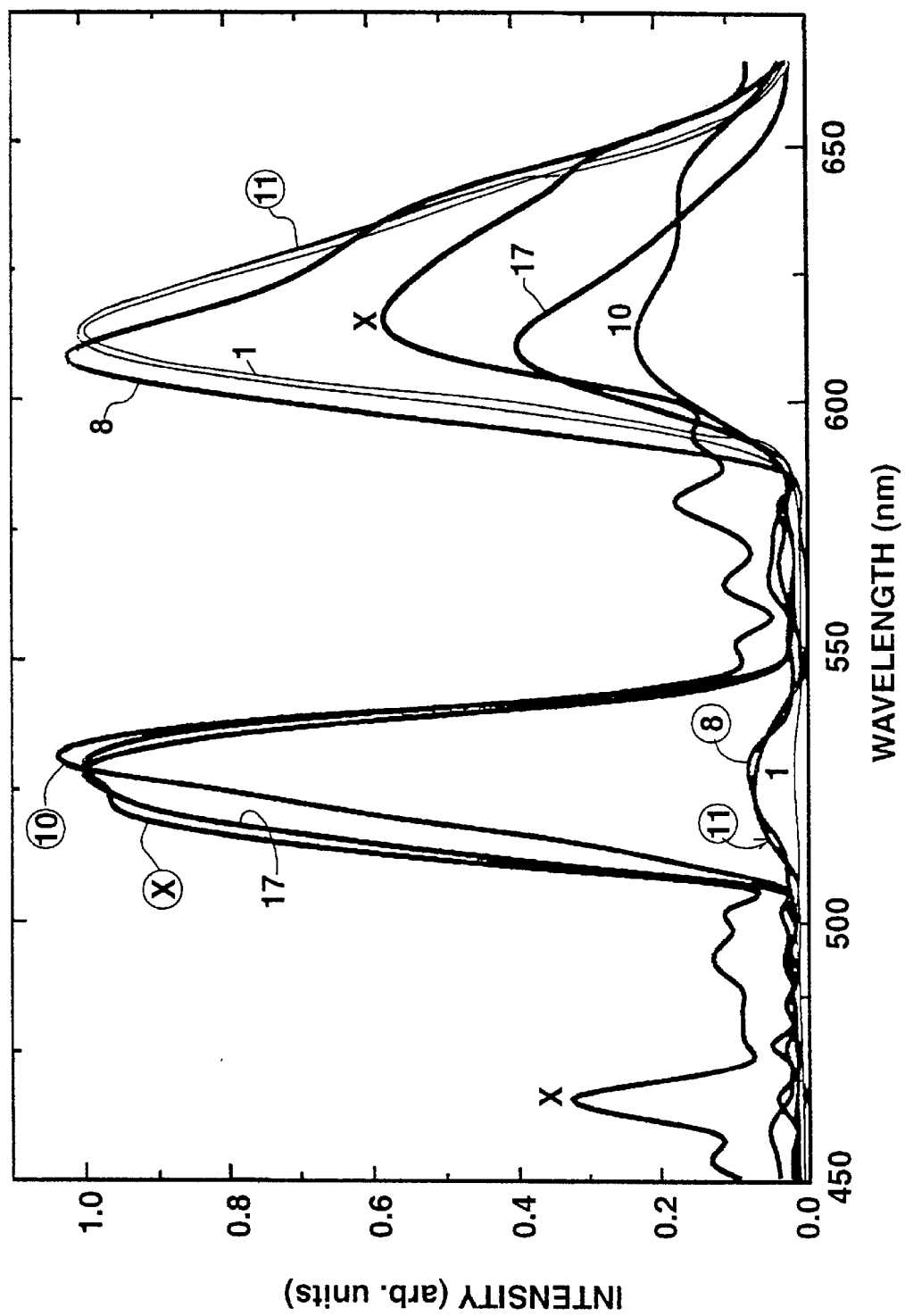
Figure 7A:
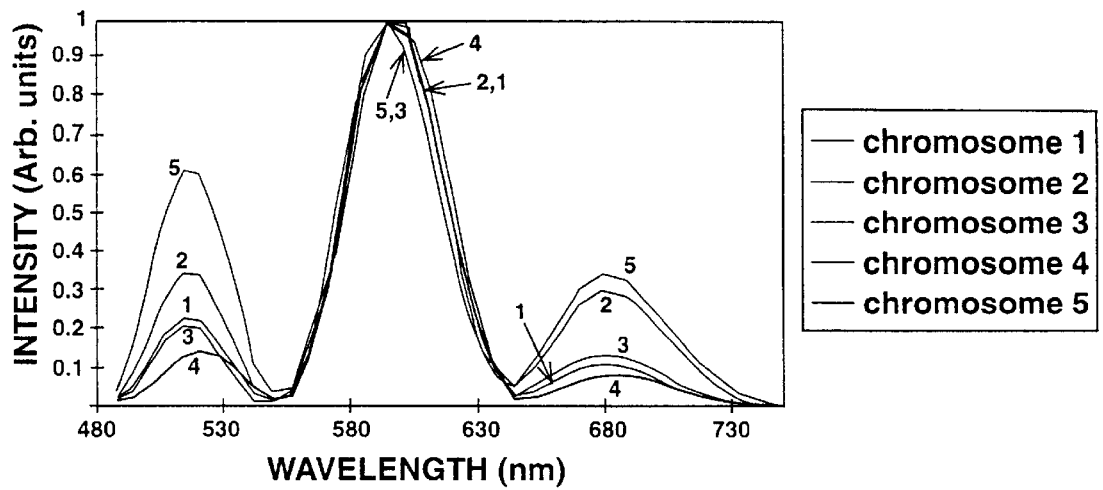
FIGS. 7a, 7b, 7c, 7d and 7e collectively show 24 normalized spectra of 24 pixels of the image of FIGS. 8a and 9a, each of the 24 pixels is derived from a different human chromosome (1–22, X and Y), each of the chromosomes was painted using a different chromosome paint as detailed in Tables 3 and 4 below.
Figure 7B:
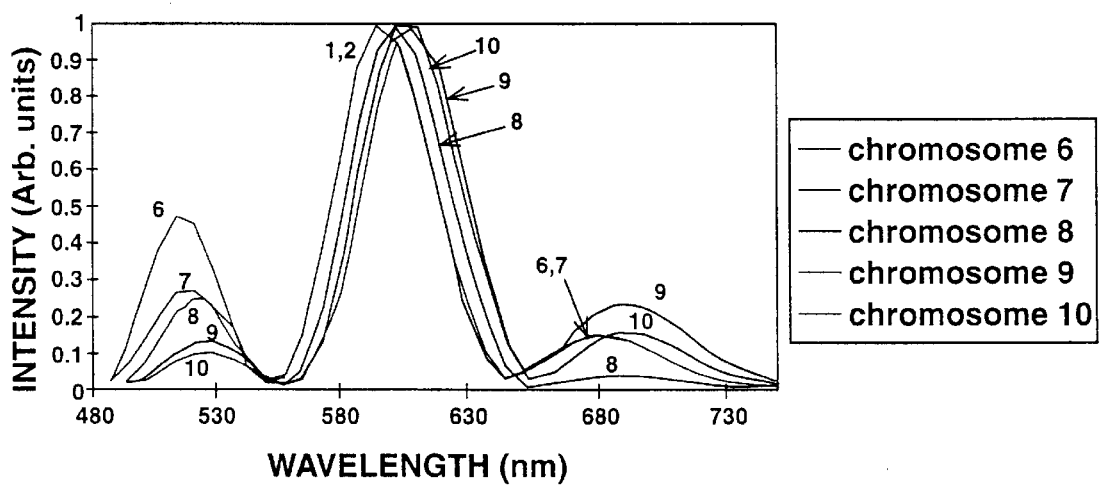
Figure 7C:
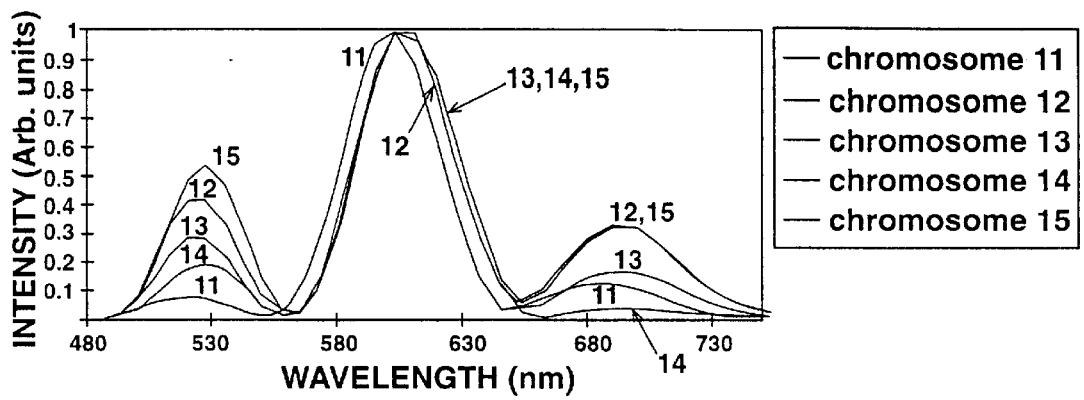
Figure 7D:
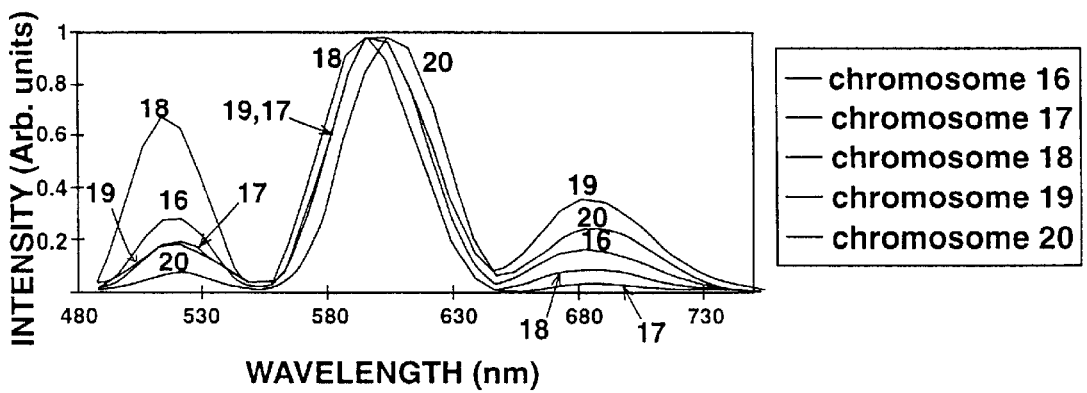
Figure 7E:
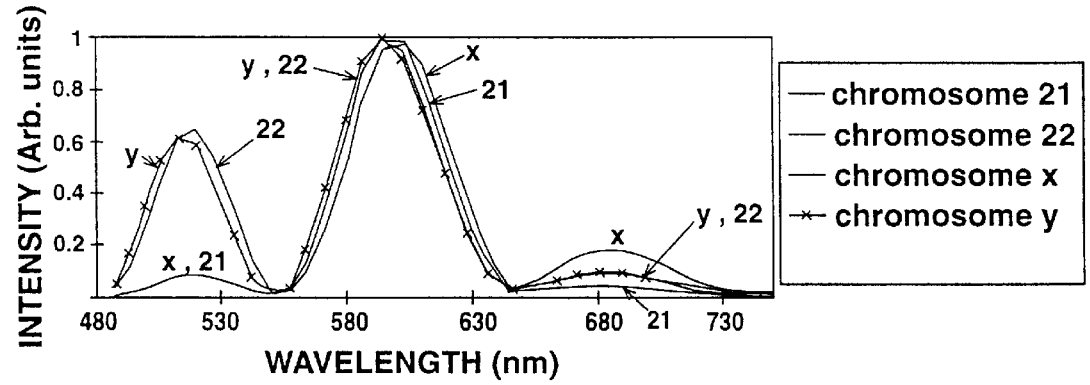
Figure 8:
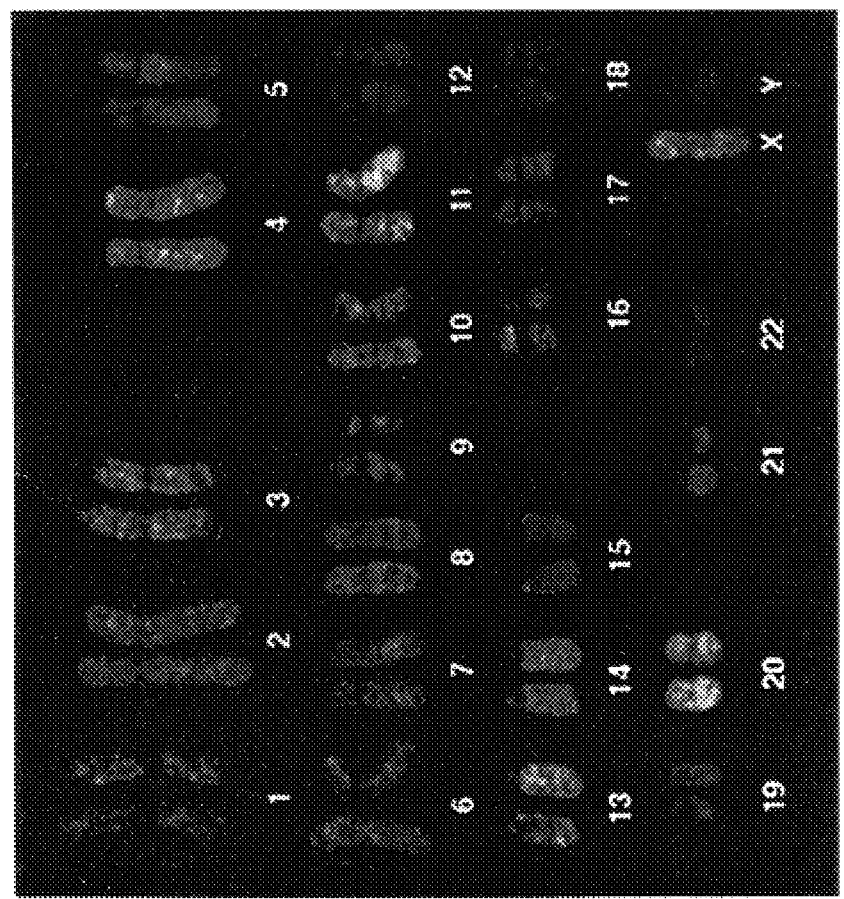
FIGS. 8a and 8b are an RGB image and a color karyotype (presented in black and white) derived from it, respectively, of the 24 human male chromosomes (1–22, X and Y) each of the chromosomes was painted using a different chromosome paint as detailed in Tables 3 and 4 below, obtained using the method of the present invention.
Figure 8:
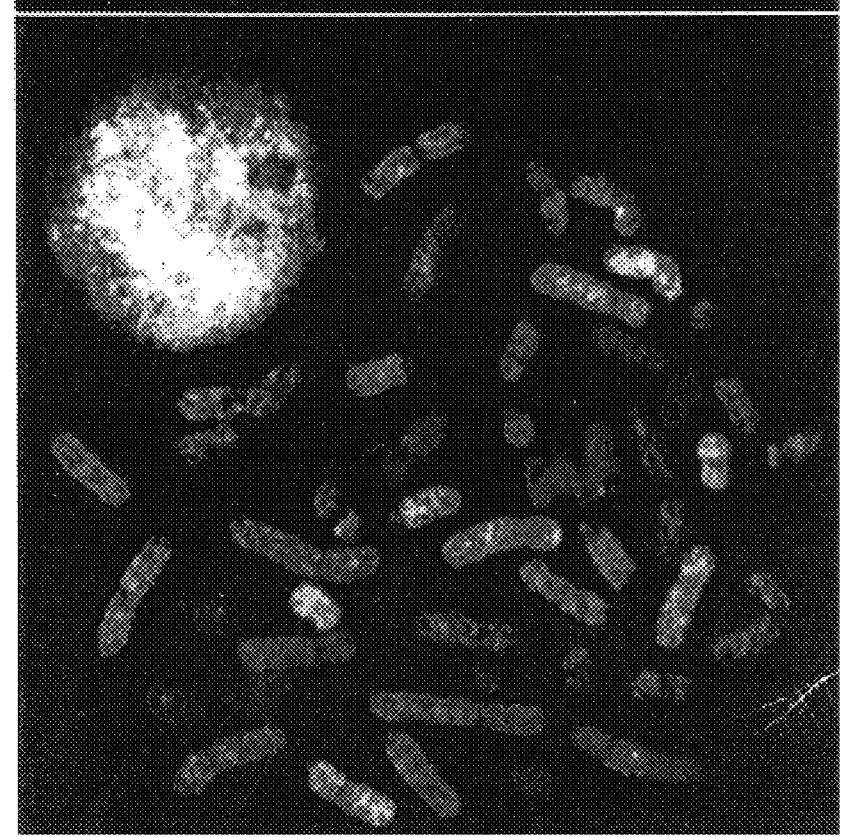

From the normalized spectral signatures of each of the six fluorophores shown in FIG. 6c, it is clear that a system based on filters measuring at a few relatively wide spectral ranges, is not able to differentiate reliably between the different probes species, because of the large overlap between the spectra. Such a system is more dependent on the absolute measurement of the intensity of each probe, and therefore it is more affected by background signals and noise. It should be further noted that spectral overlapping sometimes occurs also with auto-fluorescence originating from the cell itself. In this case too, the availability of spectral information for each pixel enables the elimination of the auto-fluorescence contribution, and yields more accurate results.

TABLE 2

| Chromosome | Fluorophore | Emission peak | Displayed color |
|---|---|---|---|
| 8 | SPECTRUM ORANGE | 588 nm | Brown (B1) |
| 10 | SPECTRUM GREEN | 538 nm | Cyan (C) |
| x | Aqua[1] | 480 nm | Blue (B2) |
| 1 | Texas-Red[2] | 615 nm | Yellow (Y) |
| 17 | FITC[3] | 525 nm | Green (G) |
| 11 | Texas-Red[2] + FITC[3] | 615, 525 nm | Red (R1) |
| backg. | DAPI[4] | | Black (B3) |

[1]obtained as labeled deoxynucleotides from Vysis, Downers Grove, IL, U.S.;
[2]conjugated via anti-digoxigenin antibody to pre hybridized digoxigenin containing probes;
[3]fluorescein-5-iso-thiocyanate, conjugated via anti-biotin antibody to pre hybridized biotin containing probes;
[4]4',6-diamidino-2-phenylindole used for counter staining.

Having measured the full spectrum of each point on the image, may also help overcome specificity problems of the probes. In fact in some cases, a probe that matches a certain chromosome DNA sequence, has also a lower specificity to a different (usually similar) sequence, and it hybridizes with a lower probability to the second sequence too. This leads to the spurious appearance of too many probes of a certain type. However, the fluorescence spectrum in the second case is very slightly shifted with respect to the first one, due to a small change in the chemical environment of the probe. The SpectraCube™ system, thanks to its spectral resolution and sensitivity, may eliminate this artifact. A similar artifact exists for probes which are not washed out during sample preparation, and contribute to false positive diagnosis. The SpectraCube™ system combined with the method of the present invention, therefore, helps lowering the risk of wrong diagnosis.

Generalizing to a large number or similar dyes, the examples of FIGS. 5a–b and 6a–c show that it is possible to detect and distinguish a large number of probes, and, provided there are small spectral differences between them, the SpectraCube™ will detect and identify them in one measurement.

It is clear to one ordinarily skilled in the art that other and/or additional known and yet to be discovered or developed fluorophores and fluorophores combinations may be used in various FISH applications as detailed above to detect large number of loci simultaneously, to paint each chromosome of a karyotype in a distinguished color, etc. A list of flourophores used in state of the art cellular and molecular biology may be found in Kasten (1993) Introduction to fluorescent probes: Properties history and applications, in Fluorescent and luminescent probes for biological research, Mason Ed. Academic Press Limited, London, pp. 24–31. It is also clear to one ordinarily skilled in the art that other labeling techniques such as for example bioluminescent and chemoluminescent and also non-fluorescent labeling strategies may be similarly applied.

Thus, using the SpectraCube™ system for FISH analysis enjoys a major advantage as follows. The SpectraCube™ system, due to its high spectral resolution, enables simultaneous detection of numerous probes, whereas using conventional means to perform FISH (e.g., using a fluorescence microscope) limits the number of probes to be used in a single hybridization to two—four probes. Therefore, employing the SpectraCube™ system for FISH analyses save effort and time. Furthermore, while employing the SpectraCube™ system for FISH analysis a smaller number of cells are required for full analysis, an important feature in cases where the number of cells to be analyzed is limited.

EXAMPLE 2

Simultaneous Visualization of all Human Chromosomes in Different Colors using Fluorescent in Situ Hybridization and Spectral Bio-imaging The emergence of multicolor FISH has broadened the applications of molecular cytogenetics in basic research and genetic diagnosis. All existing multicolor FISH techniques require the use of fluorescent probes whose emission spectra can be separated with optical filters [Ried et al., (1992) Simultaneous visualization of seven different DNA probes by in situ hybridization using combinatorial fluorescence and digital imaging microscopy. Proc. Natl. Acad. Sci. U.S.A. 89, 1388–1392; and, Ried (January 1994) Fluoreszenz in situ Hybridizierung in der genetischen Diagnostik, Faculty of theoretical medicine, Ruprecht-Karls University Heidelberg]. This requirement limits the number of dyes which can be distinguished in a given sample. According to the present invention provided is a novel approach for FISH, employing the SpectraCube™ system and the method of the present invention to measure and analyze multiple spectrally overlapping labeled probes (single and combinatorial). In this Example, spectral bio-imaging which, as delineated above, is a combination of Fourier spectroscopy, CCD-imaging and optical microscopy enabling the measurement of definitive spectral data simultaneously at all points of a biological sample, was used to visualize hybridization based multicolor bands along all (i.e., 24) types of human chromosomes and to generate a color map of the human karyotype.

For this purpose, 24 chromosome paints (1 through 22, X and Y, Table 4) each labeled with a different combination of five or less different flourophores (a through e, Table 3), (see Table 3 for the different fluorophores and their spectral characteristics and Table 4 for the assignment of the fluorophores listed in Table 3 to obtain the 24 chromosome paints), were simultaneously hybridized with human mitotic chromosome spreads of male white blood cells, prepared for hybridization essentially as described in Ried et al. [Ried et al., (1992) Simultaneous visualization of seven different DNA probes by in situ hybridization using combinatorial fluorescence and digital imaging microscopy. Proc. Natl. Acad. Sci. U.S.A. 89, 1388–1392]. Hybridized chromosomes were viewed through an inverted fluorescence microscope connected to the SpectraCube™ System and were analyzed.

TABLE 3

| Fluorophore | Symbol | Excitation (nm) |
| --- | --- | --- |
| FITC | a | 475–495 |
| Cy2 ™[1] | b | 475–495 |
| Cy3 ™[1] | c | 540–570 |
| Texas-Red | d | 540–570 |
| Cy5 ™[1] | e | 630–670 |

[1]from Amersham

TABLE 4

| Chromosome | Chromosome paint | Flourophores |
| --- | --- | --- |
| human chromosome 1 | 1 | b, c, d |
| human chromosome 2 | 2 | a, d, e |
| human chromosome 3 | 3 | a, c, e |
| human chromosome 4 | 4 | a, c, d |
| human chromosome 5 | 5 | a, b, e |
| human chromosome 6 | 6 | a, b, d |
| human chromosome 7 | 7 | b, c, e |
| human chromosome 8 | 8 | a, b, c |
| human chromosome 9 | 9 | d, e |
| human chromosome 10 | 10 | c, e |
| human chromosome 11 | 11 | c, d |
| human chromosome 12 | 12 | b, e |
| human chromosome 13 | 13 | b, d |
| human chromosome 14 | 14 | b, c |
| human chromosome 15 | 15 | a, e |
| human chromosome 16 | 16 | a, d |
| human chromosome 17 | 17 | a, c |
| human chromosome 18 | 18 | a, b |
| human chromosome 19 | 19 | e |
| human chromosome 20 | 20 | d |
| human chromosome 21 | 21 | c |
| human chromosome 22 | 22 | b |
| human chromosome X | X | c, d, e |
| human chromosome Y | Y | a |

With reference now to FIGS. 7a–e, 8a–b and 9a–b. FIGS. 7a–e show normalized spectra of 24 individual pixels, each of a different type of human chromosome (1–22, X and Y). Numbers 1–22 and letters X and Y, refer to the chromosome type of which each of the spectra presented were derived. Note that the spectrum obtained from each of the 24 human chromosomes, as shown in FIGS. 7a–e, differ from all other spectra. This difference may be large (compare, for example, the Ca. 530 nm emission peak of chromosome 15 and 11 in FIG. 7c) or small (compare, for example, the Ca. 530 nm emission peak of chromosome 22 and Y in FIG. 7e) and, in some spectral ranges may even disappear (compare, for example, the Ca. 680 nm emission peak of chromosome 22 and Y in FIG. 7e). Nevertheless, as further shown in FIGS. 7a–e, even a minor difference between very similar spectra can be detected using the SpectraCube™ system and the method of the present invention. It is however clear from this description that the ability of the method of the present invention to detect differences among spectra, to a large extent depends upon appropriate fluorophores and fluorophore combinations selected, yet, as will be appreciated by one ordinarily skilled in the art and even by one expert in the art, the ability herein demonstrated, far beyond exceeds that of any prior art cytogenetic technique.

FIG. 8a shows an RGB image of thus described painted human chromosomes, whereas FIG. 8b shows a color human karyotype derived from the painted chromosomes of FIG. 8a. Since it is not possible to literally describe 24 different colors, colored FIGS. 9a and 9b which are otherwise identical to black and white FIGS. 8a and 8b, respectively, are also enclosed. Note that each of the chromosome pairs is painted in a different color and that the color karyotype (FIG. 9b) is readily derived from the color image (FIG. 9a).

The algorithm used to obtain and display the image of FIGS. 8a and 9a was an RGB algorithm as described above and as exemplified in FIG. 4, wherein R=640–740 nm; G=550–640; and, B=530–550 nm. However to obtain a more unified image in terms of intensities, a special modification of the RGB values obtained was exercised. This modification, known in the color imaging art as "contrast stretching", [see for example, ENVI™ User's guide, The environment for visualizing images Version 1.1 July 1994

Edition, BSC limited Liability Company] includes (a) determining the distribution of each of the RGB values; (b) defining a look-up table for maximizing differences among intensities within the determined distribution; and (c) displaying the modified RGB image, now having a maximal color variation for each original different spectrum. This simple modification of the original RGB image is actually a limited version of a classification algorithm as described above. It is however clear to one ordinarily skilled in the art that other algorithms may equivalently or better suit the purpose of displaying similar images. As detailed and exemplified hereinabove (e.g., Example 1), classification mapping will enable to present any of the human chromosomes in any predetermined artificial color to obtain an even more chromosome distinctive color patterns. As further detailed above, a principal component analysis may also be found suitable, wherein each meaningful component or combinations thereof will be attributed a different predetermined artificial color. Yet, additional algorithms capable of differentiating similar spectra and attributing a different predetermined artificial color (or pseudo color) to pixels having a different spectrum may also be found suitable for color karyotyping according to the method of the present invention.

In this Example, the use of 24 different single and combinatorial probes combined from five different basic fluorophores (a through e, Table 3) was demonstrated for human color chromosome karyotyping. Nevertheless, some other species have a greater number of chromosomes, which perhaps requires the use of more complicated combinatorial probes combined of more basic fluorophores. Yet, it should be noted that chromosomes, including human chromosomes, can also be classified to size groups, which, for some applications minimize the need for as many different colors since chromosomes belonging to different size groups may be similarly colored yet easily recognized according to their relative size. This could be achieved by manual inspection, or alternatively using any morphological algorithm.

EXAMPLE 3

Detection of Multiple Chromosome Translocations in Beast Cancer Cells

As demonstrated, the method of the present invention can provide a complete color karyotype of normal blood cells. In many cases conventional karyotyping (e.g., using G-banding or R-banding techniques) is used to detect chromosomal aberrations such as translocations associated with genetic disorders (e.g., 21q22 trisomy in Down's syndrome, chromosome 18 (or a fragment thereof) trisomy and chromosome 13 (or a fragment thereof) trisomy) or malignancies (e.g., a translocation between the distal ends of chromosomes 9 and 22 in leukocytes from patients with chronic myelogenous leukemia and, a chromosomes 8 and 14 translocation in lymphocytes of patients with Burkitt's lymphoma). In this Example the capabilities of the SpectraCube™ system combined with the method of the present invention to detect multiple chromosome translocations in breast cancer cells is demonstrated.

Figure 10:
FIGS. 10a and 10b are a DAPI R-banding presentation obtained with a conventional fluorescence microscope and an RGB color karyotype obtained using the chromosome paints as in FIGS. 9a–b and the method of the present invention (presented in black and white), respectively, of a female breast cancer cell chromosome spread.
Figure 10:
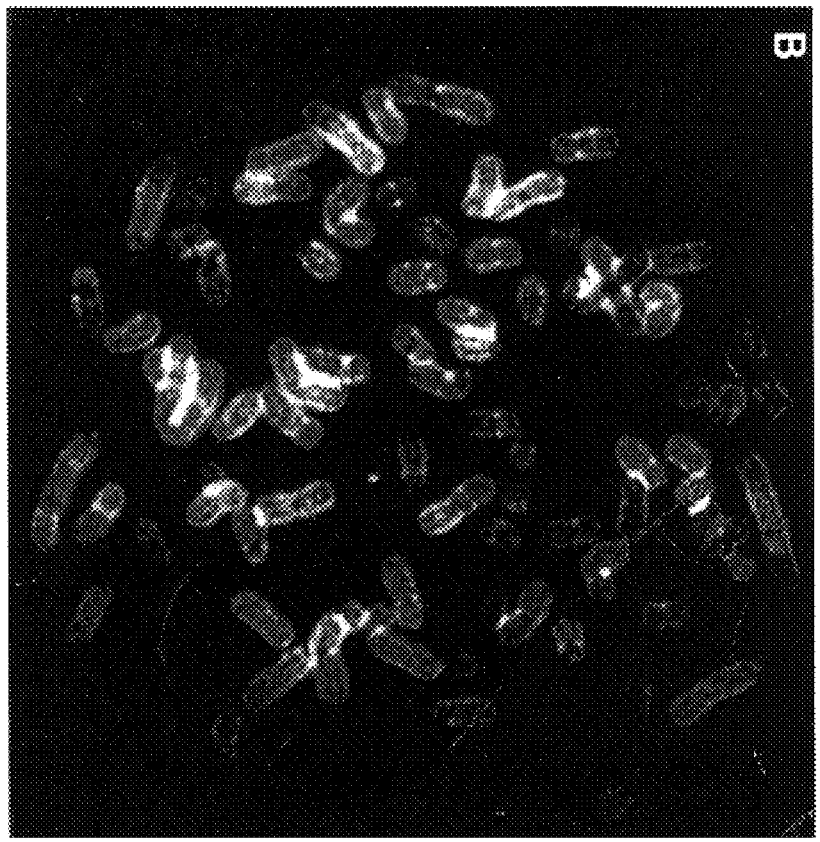
Figure 11:
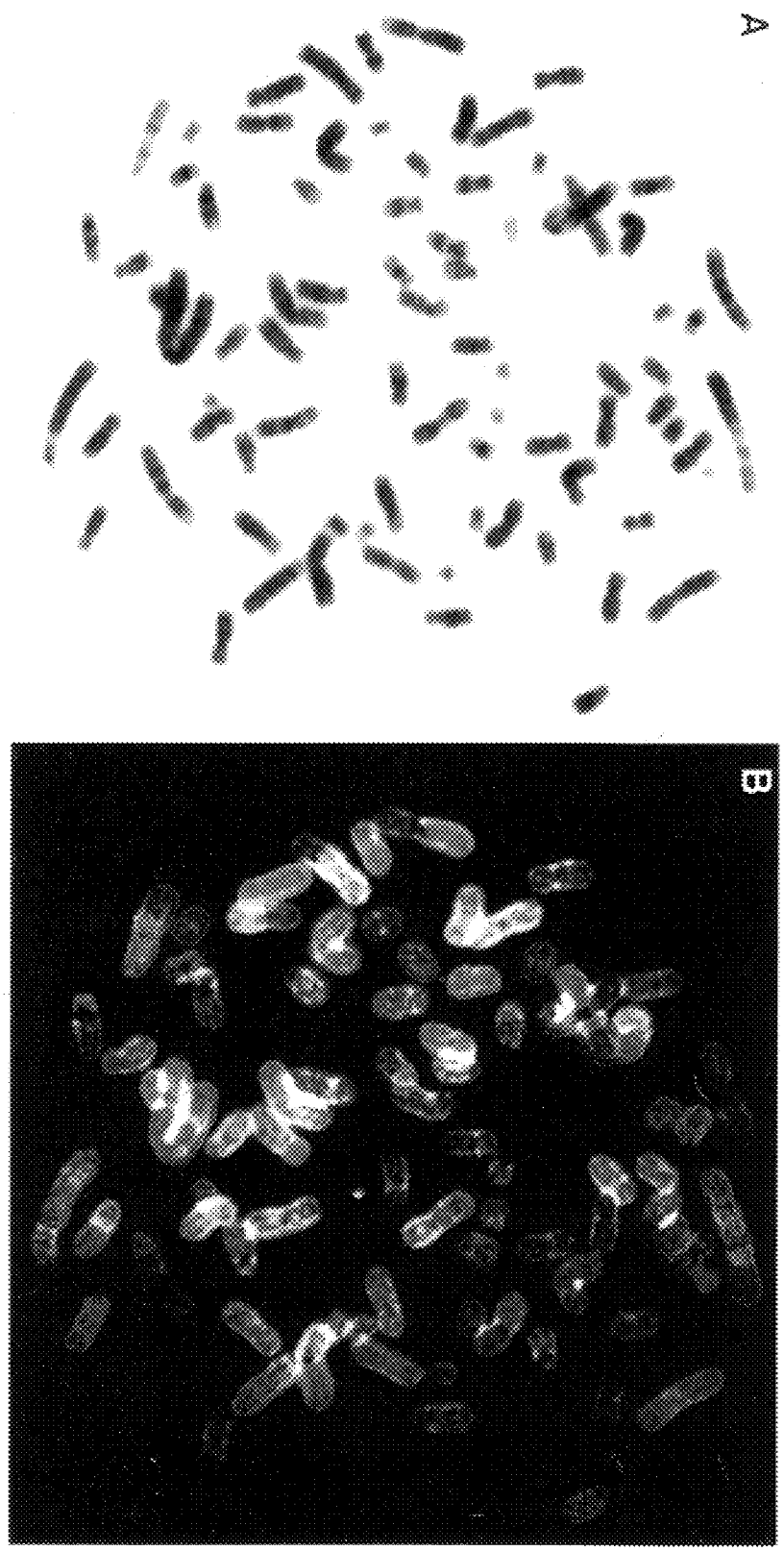
FIGS. 11a and 11b are an original and more clear presentation and a color presentation of FIGS. 10a and 10b, respectively.
Figure 12:
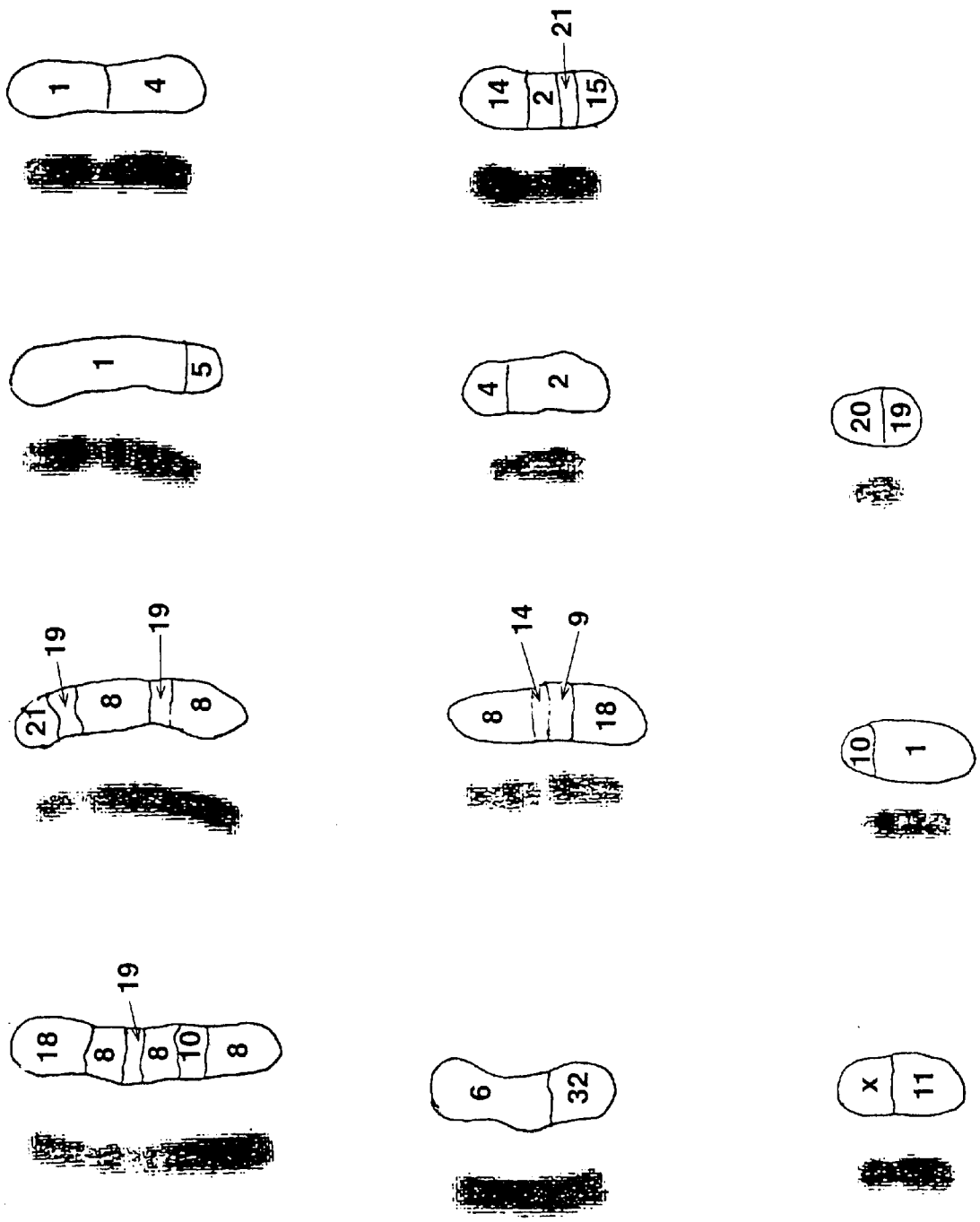
FIG. 12 is a comparative presentation of the DAPI R-banded and an interpreted outline of the painted translocated chromosomes presented in FIGS. 11a (left) and 11b (right), respectively, as was determined from FIG. 11b and interpreted using the color karyotype shown in FIG. 9b.
Figure 13:
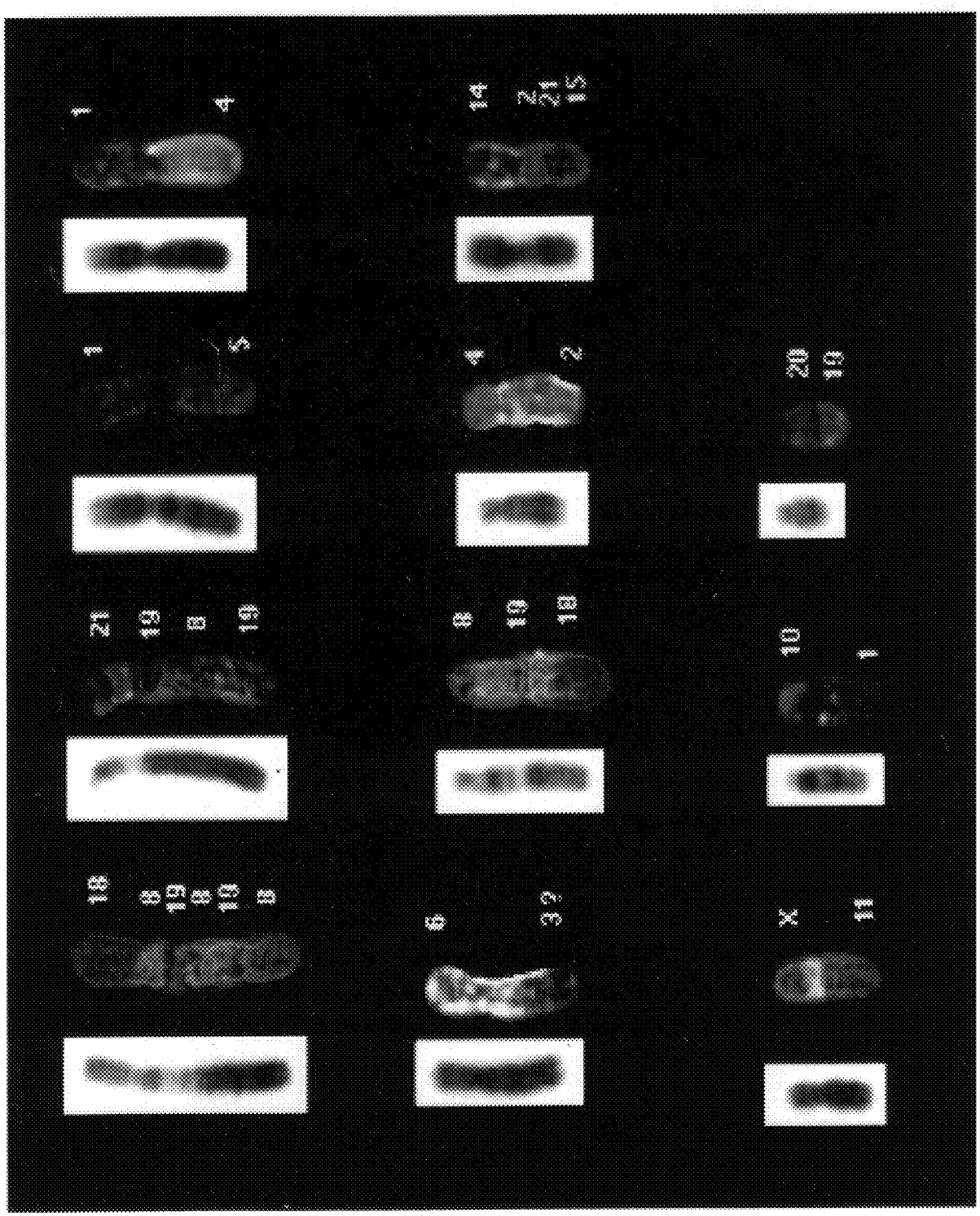
FIGS. 13 is a color presentation of FIG. 12.

With reference now to FIGS. 10a–b, 11a–b 12 and 13. Chromosome spreads of breast cancer cells were hybridized with the 24 chromosome paints (1 through 22, X and Y) as detailed in tables 3 and 4 above and were spectrally imaged as detailed under Example 2 above. FIGS. 10a and 11a show DAPI R-banding of a chromosome spread as was photographed using a conventional fluorescence microscope. It will be appreciated that although the resulting karyotype is abnormal to a large extent, it is impossible to identify specific translocations of chromosomes in FIGS. 10a and 11a. FIGS. 10b and 11b show (in black and white and color, respectively) an RGB image of the same spread as was obtained using the SpectraCube™ system and the method of the present invention. When compared with FIGS. 9a–b, presenting a normal human karyotype derived under otherwise identical experimental conditions, it is apparent that many of the aberrations containing chromosomes shown in FIGS. 10b and 11b contain parts of various normal human chromosomes. The translocated chromosomes (right) of FIGS 10b and 11b, along with the R-banded chromosomes (left) are shown in FIGS. 12 and 13. Note that some of the translocated chromosomes shown in FIGS. 12 and 13 include fragments originated from two, three and even four different chromosomes. Since specific chromosome translocations and other chromosomal aberrations (e.g., gene amplification) were previously associated with early or stage specific malignancies and, since the method of the present invention tremendously increases the ability to detect and characterize such translocations and other aberrations, the ability of early detection and stage classification of malignancies exercising the method of the present invention will be benefited. Furthermore, using the method of the present invention will enable to establish yet new chromosome specific aberrations (e.g., translocations) recurrently associated with specific malignancies and eventually to provide a comprehensive guide for such translocations. In addition, such recurrent aberrations may lead to the isolation of genes that by being activated or alternatively inactivated are associated with the malignant processes.

In this context it is important to notice that the fluorophores employed in this and the former Example 2 (as listed in Table 3 and shown in FIGS. 7a–c) collectively emit in the 480–730 nm range. Thus DAPI can be simultaneously used for counter staining since its emission is in the blue, well below this spectral range.

Thus, as shown in Figures 10a–b, 11a–b, 12 and 13, it is possible to simultaneously observe the very same chromosome spreads using the conventional monochromatic R-banding approach and the multi-color approach of the present invention. It is clear that the SpectraCube™ system is capable of providing a conventional DAPI R-banding image by limiting the examined spectral range to blue. Thus, for a comparative purpose a single chromosome spread may be viewed using the SpectraCube™ system and the method of the present invention as a DAPI R-banded karyotype as well as a color karyotype. Hence, when chromosome translocation events are studied according to the method of the present invention the DAPI R-banded karyotype can provide additional information and to precisely point out which region(s) (i.e., bands) of any specific chromosome are involved in a specific translocation event.

EXAMPLE 4

Additional Fish Applications

From the above descriptions it is clear that (1) several types of probes may be used for FISH, these include loci specific probes, chromosome paints and whole genomes; (2) the analyzed chromosomes may be during interphase, mitosis or meiosis; and, (3) dozens of probes of all types may be simultaneously hybridized to the chromosomes and, provided that each of the probes has a somewhat different spectrum, the SpectraCube™ system as used according to the method of the present invention can spectrally detect each of the probes and present its spatial arrangement by attributing pixels presenting each of the spectra an RGB color (i.e., pseudocolor) or a predetermined artificial color.

Thus, for example if the method of the present invention is to be used for mapping a newly isolated gene(s) (or other DNA sequences), a single procedure may be employed to map the gene(s) to their chromosomal bands. Exemplified for two new genes, to this end 26 different probes may be prepared as follows: 24 chromosome paints and two loci specific probes (i.e., the newly isolated genes fluorescently labeled). The probes are then mixed and simultaneously hybridized preferably to mitotic chromosomes which are also DAPI counter stained. The result is a 24 (for a male, or 23 for a female) color karyotype, similar to the one presented in FIG. 9b, on which two loci specific signals (dots attributed to the loci specific probes) in yet two different colors point out the chromosome locations of the newly isolated genes which are then associated with a specific chromosomal band by generating an R-banded image as explained above.

In many cases, few loci specific probes are mapped to a single chromosomal band, yet which is distal and which is proximal is not established. Using the method of the present invention to simultaneously detect each of the few probes as each appears in a different RGB or artificial color, will, in many cases, enable to determine the relative arrangement of closely mapped sequences.

The SpectraCube™ system and the method of the present invention may also be used to detect interphase chromosome three dimensional arrangements. The reader is referred again to FIGS. 8a and 9a. On the upper right corner presented is a nuclei during interphase (marked NI) hybridized with the chromosome paints listed in Table 4 above. Examination of the color pattern of this nuclei reveals a unique feature. Note for example that both the chromosome 2 pair (in red) are located in the lower part of the nuclei and that the chromosome 6 pair (in purple) are both located in the opposite pole. Little is so far known about the chromosome organization during interphase, yet it is reasonable to suspect that changes occur in the chromosome organization during interphase in malignant cells. Thus, the method of the present invention may be of great value for early detection of various malignancies, defining the stage of a malignant disease, and hence better adjust a treatment to examined patients, etc. It should be noted that using the SpectraCube™ system combined with the method of the present invention and a three dimensional reconstruction means (e.g., a confocal microscope) may be used to extract three dimensional information of chromosome organization during interphase.

Many cancers and genetic disorders are characterized by chromosome deletions, translocations and other rearrangements and gross abnormalities (e.g., gene amplification). As demonstrated in Example 3 above, using the method of the present invention will enhance the ability to detect such abnormalities. Furthermore, it is clear that the method of the present invention is highly suitable for comparative genomic hybridization (CGH) and for reverse chromosome painting as described above.

One of the common chromosomal aberrations is associated with Down's-syndrome. It was long ago established that Down's syndrome results due to trisomy of chromosome 21. More careful examination revealed that a specific region of chromosome 21 (21q22) is always associated (i.e., appears in trisomy) with this common syndrome. However, in some cases the karyotype of individuals affected with Down's syndrome is apparently normal as determined by conventional G- or R-banding karyotyping techniques. The widely accepted explanation to this phenomenon is that in these cases the trisomy is of a fragment derived from the 21q22 chromosome region which fragment is small and below the resolution of the conventional banding techniques. However, using the SpectraCube™ system combined with the method of the present invention will enable to detect these so far undetectable chromosome 21 tisomies in embryonic cells obtained for example via chorionic villi sampling and to enable a more educated genetic counseling to high risk women. It should be noted that chromosome 13 and chromosome 18 or fragments thereof were also reported to appear in trisomies resulting in birth of strikingly abnormal children and that the method of the present invention can be similarly applied for a prenatal diagnosis of these devastating chromosome 13 or 18 trisomies.

The method of the present invention, combined with the rapidly developing techniques of separating embryonic cells from peripheral blood of a pregnant woman will be of great value for low-risk prenatal karyotyping for the detection of chromosome 21 trisomies and other, less frequent chromosome abnormalities.

Using the SpectraCube™ system and the method of the present invention combined with chromosome telomeres specific probes, each of the telomers (48 in human males, 46 in females) appears in a different color, will enable a comparative study of all telomeres in an examined species.

In the study of evolutionary related species and in the study of model systems (for example mouse as a model system for human) it is in many cases required to obtain comparative genome maps in which chromosomes of two or more species are aligned according to their sequence similarities and thus their chromosome-borne genetic information. Using the method of the present invention will facilitate obtaining such comparative maps. Consider for example the preparation of a human-mouse chromosome comparative map. For this purpose a complete set of chromosome paints of one of the species (e.g., human) are to be simultaneously hybridized with chromosome spreads of the other species (mouse in the given example) and analyzed as described above. The result is an image of the mouse karyotype painted with the human chromosome paints. Thus, an alignment can be made between the karyotypes of the two species.

Many other applications for FISH were so far described in the arts literature. One example is in the study of gene expression wherein by using loci specific probes hybridized with interphase nuclei obtained at intervals from asynchronized cell culture one can determine their order of replication (i.e., replicated genes appear ad four dots and non-replicated genes appear as two dots), wherein, as a rule of thumb, early replicating genes are expressed in the examined cells and late replicating genes are not. The method of the present invention is highly suitable for this type of analysis since dozens of probes each having a slightly different spectrum can be analyzed simultaneously in a single hybridization followed by a single imaging step to detect them all. In fact the method of the present invention can be used for any FISH application so far described or yet to be described.

While the invention has been described with respect to a limited number of embodiments, it will be appreciated that many variations, modifications and other applications of the invention may be made.

What is claimed is:

1. A spectral bio-imaging method characterized by high spatial and high spectral resolutions, the method comprising the steps of:

(a) preparing a sample to be spectrally imaged;
(b) viewing said sample through an optical device, said optical device being optically connected to an imaging spectrometer, said optical device and said imaging spectrometer being for obtaining a spectrum of each pixel of said sample by:
  (i) collecting incident light simultaneously from all pixels of said sample using collimating optics;
  (ii) passing said incident collimated light through an interferometer system having a number of elements, so that said light is first split into two coherent beams which travel in different directions inside said interferometer and then said two coherent beams recombine to interfere with each other to form an exiting light beam;
  (iii) passing said exiting light beam through a focusing optical system which focuses said exiting light beam on a detector having a two-dimensional array of detector elements, so that at each instant each of said detector elements is the image of one and always the same pixel of said sample for the entire duration of the measurement, so that the real image of the sample is stationary on the plane of the detector array and at any time during the measurement the image is still visible and recognizable, and so that each of said detector elements produces a signal which is a particular linear combination of light intensity emitted by said pixel at different wavelengths, wherein said linear combination is a function of the instantaneous optical path difference;
  (iv) translating one or more of said elements of said interferometer system, so that said optical path difference between said two coherent beams generated by said interferometer system is scanned simultaneously for all said pixels of said sample; and
  (v) recording signals of each of said detector elements as function of time using a recording device to form a first spectral cube of data; and
(c) interpreting said first spectral cube of data using a mathematical algorithm.

2. A method as in claim 1, further comprising the step of:
(d) displaying a map of said interpreted spectral cube of data.

3. A method as in claim 1, wherein said optical device is a fluorescence microscope.

4. A method as in claim 1, wherein said collimated light is a fluorescence light emitted from said sample.

5. A method as in claim 4, wherein said collimated light emitted from said sample is an administered probe fluorescence.

6. A method as in claim 1, wherein said light originates from a source selected from the group consisting of laser, white light, filtered light, ultraviolet light and a light having a small wavelength range.

7. A method as in claim 1, wherein said light originates from a multiplicity of light sources, said sources operate simultaneously.

8. A method as in claim 1, wherein said light originates from a multiplicity of light sources, said sources operate successively.

9. A method as in claim 1, wherein said two-dimensional array is selected from the group consisting of a video rate CCD, a cooled high dynamic range CCD, an intensified CCD and a time gated intensified CCD.

10. A method as in claim 1, wherein said sample is selected from the group consisting of a cell during interphase, a cell during mitosis and a cell during meiosis.

11. A method as in claim 10, wherein said cell is from a human.

12. A method as in claim 10, wherein said cell is selected from the group consisting of a cancerous cell, a blood cell, a fetal cell and a cell suspected of being malignant.

13. A method as in claim 1, wherein said sample is a cell, said light is induced by a probe, said probe binds to a specific cellular constituent, the method is for detecting the presence or the level of said cellular constituent.

14. A method as in claim 13, wherein said probe includes a conjugated fluorescent moiety and said induction is a fluorescence light emission of said fluorescent moiety.

15. A method as in claim 14, wherein said probe further includes a nucleic acid molecule, the method is for detecting the presence or the level of a cellular nucleic acid hybridizing with said nucleic acid molecule.

16. A method as in claim 15, wherein said cellular nucleic acid is selected from the group consisting of deoxyribonucleic acid and ribonucleic acid.

17. A method as in claim 14, wherein said fluorescent moiety is selected from the group consisting of Aqua, Texas-Red, FITC, rhodamine, rhodamine derivative, fluorescein, fluorescein derivative, cascade blue and any combination thereof.

18. A method as in claim 1, wherein said mathematical algorithm is a point operation analysis of said spectrum of each of said pixels in said sample.

19. A method as in claim 18, wherein said point operation analysis includes mapping said spectrum of each of said pixels in said sample into a scalar according to a transformation function.

20. A method as in claim 18, wherein said point operation analysis includes mapping said spectrum of each of said pixels of said sample into another spectrum according to a transformation function.

21. A method as in claim 1, wherein said mathematical algorithm is a morphological analysis.

22. A method as in claim 1, wherein said mathematical algorithm is a similarity mapping analysis for computing for each of said pixels in said sample a spectral difference from a reference spectrum.

23. A method as in claim 22, wherein said similarity mapping analysis results in generating a gray level or a pseudocolor image, in which bright pixels correspond to a small spectral difference and dark pixels correspond to a large spectral difference.

24. A method as in claim 22, wherein said similarity mapping analysis results in generating a gray level or a pseudocolor image, in which bright pixels correspond to a large spectral difference and dark pixels correspond to a small spectral difference.

25. A method as in claim 22, wherein said spectral difference is a scalar defined as the integral over a predefined wavelength range of the absolute value of the difference between said spectrum of each of said pixels and said reference spectrum.

26. A method as in claim 1, wherein said mathematical algorithm is a classification mapping analysis computing for said spectrum of each of said pixels a spectral difference from several reference spectra.

27. A method as in claim 26, wherein said classification mapping analysis results in generating a multicolor image, in which groups of pixels having a predetermined maximal spectral differences from one of said several reference spectra are colored with a predetermined artificial color.

28. A method as in claim 26, wherein said spectral difference is a scalar defined as the integral over a predefined wavelength range of the absolute value of the difference between said spectrum of each of said pixels and one of said several reference spectra.

29. A method as in claim 1, wherein said mathematical algorithm is a principal component analysis.

30. A method as in claim 29, wherein said principal component analysis includes:
 (a) building a covariant matrix for all of said pixels and said wavelengths of said measurement, including wavelengths of exciting sources when multiple wavelengths are used;
 (b) diagonalizing said covariant matrix and finding all independent orthogonal spectral base elements;
 (c) finding which of said base elements or a combination thereof tag certain features in said sample.

31. A method as in claim 1, wherein said mathematical algorithm is a linear combination analysis.

32. A method as in claim 31, wherein said linear combination analysis includes applying an arithmetical function between corresponding wavelengths of corresponding pairs of pixels belonging to said first spectral cube of data and to a second spectral cube of data, to obtain a resulting third spectral cube of data.

33. A method as in claim 31, wherein said linear combination analysis is for a purpose selected from the group consisting of averaging two spectral cubes of data and time changes follow-up and spectral normalization.

34. A method as in claim 36, wherein said linear combination analysis includes applying a given scalar to every wavelength of said spectra of each of said pixels by an arithmetical function, said function is selected from the group consisting of addition, subtraction, multiplication, division and combinations thereof.

35. A method as in claim 31, wherein said linear combination analysis is for background subtraction in which a spectrum of a pixel located in a background region of said sample is subtracted from said spectra of said pixels of said sample.

36. A method as in claims 31, wherein said linear combination analysis is for a calibration procedure in which a spectrum measured prior to said viewing said sample is for dividing said spectra of said pixels of said sample.

37. A method as in claim 1, wherein said mathematical algorithm is an optical density analysis.

38. A method as in claim 37, wherein said optical density analysis is for obtaining an interpreted image which is an optical density map.

39. A method as in claim 1, wherein said mathematical algorithm computes a Red-Green-Blue color image using predefined wavelength ranges.

40. A method as in claim 39, wherein said Red-Green-Blue color image is modified by a contrast stretching algorithm.

41. A method as in claim 1, wherein said mathematical algorithm computes a ratio between intensities at two different wavelengths for each of said spectra of said pixels.

42. A method as in claim 1, wherein said mathematical algorithm computes a ratio between intensities at two different wavelengths for each of said spectra of said pixels and paints each of said pixels in a lighter or darker artificial color, according to said computed ratio.

43. A method as in claim 1, wherein the method is for spectral identification of multiple fluorophores administered to said sample.

44. A fluorescent in situ hybridization method comprising the steps of:
 (a) providing a cell nuclei having chromosomes, said chromosomes being hybridized with at least one nucleic acid probe, each of said at least one nucleic acid probe including at least one nucleic acid molecule, each of said at least one nucleic acid molecule being labeled with at least one fluorophore;
 (b) viewing said cell nuclei through a fluorescence microscope, said fluorescence microscope being optically connected to an imaging spectrometer, said fluorescence microscope and said imaging spectrometer being for obtaining a spectrum of each pixel of said cell nuclei by:
  (i) collecting incident light simultaneously from all pixels of said cell nuclei using collimating optics;
  (ii) passing said incident collimated light through an interferometer system having a number of elements, so that said light is first split into two coherent beams which travel in different directions inside said interferometer and then said two coherent beams recombine to interfere with each other to form an exiting light beam;
  (iii) passing said exiting light beam through a focusing optical system which focuses said exiting light beam on a detector having a two-dimensional array of detector elements, so that at each instant each of said detector elements is the image of one and always the same pixel of said cell nuclei for the entire duration of the measurement, so that the real image of the cell nuclei is stationary on the plane of the detector array and at any time during the measurement the image is still visible and recognizable, and so that each of said detector elements produces a signal which is a particular linear combination of light intensity emitted by said pixel at different wavelengths, wherein said linear combination is a function of the instantaneous optical path difference;
  (iv) rotating or translating one or more of said elements of said interferometer system, so that said optical path difference between said two coherent beams generated by said interferometer system is scanned simultaneously for all said pixels of said cell nuclei; and
  (v) recording signals of each of said detector elements as function of time using a recording device to form a first spectral cube of data; and
 (c) interpreting said first spectral cube of data using a mathematical algorithm.

45. A method as in claim 44, wherein said at least one nucleic acid molecule is selected from the group consisting of at least one locus, at least one fragmented chromosome, at least one yeast artificial chromosome including an insert, at least one plasmid including an insert, at least one cosmid including an insert, at least one phagemid including an insert, at least one viral vector including an insert, a complete genome of a species, a complete genome of a cancerous tissue and combinations thereof.

46. A method as in claim 44, wherein said at least one fluorophore is at least one fluorescent combinatorial dye.

47. A method as in claim 44, wherein said cell nuclei is selected from the group consisting of a cell nuclei during interphase, a cell nuclei during mitosis and a cell nuclei during meiosis.

48. A method as in claim 44, wherein the number of nucleic acid probes is selected from the group of numbers consisting of one, two, three, four, five, six, seven, eight, nine, ten, eleven, twelve, thirteen, fourteen, fifteen, sixteen, seventeen, eighteen, nineteen, twenty, twenty one, twenty two, twenty three, twenty four and higher than twenty four, each of said probes includes a different fluorophore or a different combination of said fluorophores.

49. A method as in claim 44, wherein said chromosomes are selected from the group consisting of interphase chromosomes, chromosomes during mitosis and chromosomes during meiosis.

50. A method as in claim 44, wherein said mathematical algorithm is a point operation analysis of said spectrum of each of said pixels in said cell nuclei.

51. A method as in claim 50, wherein said point operation analysis includes mapping said spectrum of each of said pixels in said cell nuclei into a scalar according to a transformation function.

52. A method as in claim 51, wherein said point operation analysis includes mapping said spectrum of each of said pixels of said cell nuclei into another spectrum according to a transformation function.

53. A method as in claim 44, wherein said mathematical algorithm is a morphological analysis, said morphological analysis determines the relative size of said chromosomes in said cell nuclei.

54. A method as in claim 44, wherein said mathematical algorithm is a classification mapping analysis computing for said spectrum of each of said pixels a spectral difference from at least one reference spectrum.

55. A method as in claim 54, wherein said classification mapping analysis results in generating a multicolor image, in which groups of pixels having a predetermined maximal spectral differences from one of said several reference spectra are colored with a predetermined artificial color.

56. A method as in claim 55, wherein said spectral difference is a scalar defined as the integral over a predefined wavelength range of the absolute value of the difference between said spectrum of each of said pixels and one of said several reference spectra.

57. A method as in claim 44, wherein said mathematical algorithm is a principal component analysis.

58. A method as in claim 57, wherein said principal component analysis includes:

(a) building a covariant matrix for all of said pixels and said wavelengths of said measurement, including wavelengths of exciting sources when multiple wavelengths are used;

(b) diagonalizing said covariant matrix and finding all independent orthogonal spectral base elements;

(c) finding which of said base elements or a combination thereof tag certain features in said cell nuclei.

59. A method as in claim 44, wherein said mathematical algorithm is a linear combination analysis.

60. A method as in claim 59, wherein said linear combination analysis is for spectral normalization.

61. A method as in claim 59, wherein said linear combination analysis includes applying a given scalar to every wavelength of said spectra of each of said pixels by an arithmetical function, said function is selected from the group consisting of addition, subtraction, multiplication, division and combinations thereof.

62. A method as in claim 59, wherein said linear combination analysis is for background subtraction in which a spectrum of a pixel located in a background region of said cell nuclei is subtracted from said spectra of said pixels of said cell nuclei.

63. A method as in claim 59, wherein said linear combination analysis is for a calibration procedure in which a spectrum measured prior to said viewing said cell nuclei is for dividing said spectra of said pixels of said cell nuclei.

64. A method as in claim 44, wherein said mathematical algorithm computes a Red-Green-Blue color image using predefined wavelength ranges.

65. A method as in claim 64, wherein said Red-Green-Blue color image is modified by a contrast stretching algorithm.

66. A method as in claim 44, wherein said mathematical algorithm computes a ratio between intensities at two different wavelengths for each of said spectra of said pixels.

67. A method as in claim 44, wherein said mathematical algorithm computes a ratio between intensities at two different wavelengths for each of said spectra of said pixels and paints each of said pixels in a lighter or darker artificial color, according to said computed ratio.

* * * * *